United States Patent
Lakkaraju et al.

(10) Patent No.: US 10,124,008 B2
(45) Date of Patent: Nov. 13, 2018

(54) USE OF INHIBITORS OF ACID SPHINGOMYELINASE TO TREAT ACQUIRED AND INHERITED RETINAL DEGENERATIONS

(71) Applicant: Wisconsin Alumni Research Foundation, Madison, WI (US)

(72) Inventors: Aparna Lakkaraju, Madison, WI (US); Kimberly A. Toops, Sun Prairie, WI (US); Li Xuan Tan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/746,221

(22) Filed: Jun. 22, 2015

(65) Prior Publication Data

US 2015/0366876 A1 Dec. 24, 2015

Related U.S. Application Data

(60) Provisional application No. 62/015,753, filed on Jun. 23, 2014.

(51) Int. Cl.
| | |
|---|---|
| *A61K 31/55* | (2006.01) |
| *A61K 31/136* | (2006.01) |
| *A61K 9/00* | (2006.01) |
| *A61K 31/454* | (2006.01) |
| *A61K 31/445* | (2006.01) |
| *A61K 45/06* | (2006.01) |
| *A61K 31/135* | (2006.01) |
| *A61K 31/137* | (2006.01) |
| *A61K 31/138* | (2006.01) |
| *A61K 31/343* | (2006.01) |
| *A61K 31/4422* | (2006.01) |
| *A61K 31/451* | (2006.01) |
| *A61K 31/4525* | (2006.01) |
| *A61K 31/46* | (2006.01) |
| *A61K 31/5415* | (2006.01) |
| *A61K 31/675* | (2006.01) |

(52) U.S. Cl.
CPC .......... *A61K 31/55* (2013.01); *A61K 9/0048* (2013.01); *A61K 31/135* (2013.01); *A61K 31/136* (2013.01); *A61K 31/137* (2013.01); *A61K 31/138* (2013.01); *A61K 31/343* (2013.01); *A61K 31/445* (2013.01); *A61K 31/4422* (2013.01); *A61K 31/451* (2013.01); *A61K 31/454* (2013.01); *A61K 31/4525* (2013.01); *A61K 31/46* (2013.01); *A61K 31/5415* (2013.01); *A61K 31/675* (2013.01); *A61K 45/06* (2013.01)

(58) Field of Classification Search
CPC .............................. A61K 31/55; A61K 31/136
See application file for complete search history.

(56) References Cited

FOREIGN PATENT DOCUMENTS

| WO | 9718815 A2 | 5/1997 |
|---|---|---|
| WO | 0007584 A2 | 2/2000 |
| WO | 2005097121 A1 | 10/2005 |
| WO | 2009023299 A2 | 2/2009 |

OTHER PUBLICATIONS

Van Leeuwen et al. Ophthalmology, 2004, vol. 111, pp. 1169-1175.*
Kolzer et al. FEBS Letters, 2004, Iss. 559, pp. 96-98.*
Opreanu et al. Diabetes, 2011, vol. 60, pp. 2370-2378.*
Ambati, et al., Mechanisms of age-related macular degeneration, Neuron, 2012, 75(1), 26-39.
Arroyo, A 76-Year-Old Man With Macular Degeneration, JAMA, 2006, 295(20):2394-2406.
Barmada, et al., Autophagy induction enhances TDP43 turnover and survival in neuronal ALS models, Nature Chemical Biology, 2014, 10, 677-685.
Bentley, et al., Tamoxifen Retinopathy: A Rare But Serious Complication, British Medical Journal, 1992, 304:495-496.
Cunningham, et al., Clofazamine-Induced Generalized Retinal Degeneration, Retina, 1990, 10:131-134.
Doukas, et al., Topical administration of a multi-targeted kinase inhibitor supresses choroidal neovascularization and retinal edema, Journal of Cellular Physiology, 2008, 216(1), 29-37.
Edward, et al., Amelioration of Light-Induced Retinal Degeneraiton by a Calcium Overload Blocker, Arch. Ophthalmol., 1991, 109:554-562.
Ewe, et al., Bilateral Maculopathy Associated with Sertraline, Australasian Psychiatry, 2014, 22(6):573-575.
Gammons, Topical antiangiogenic SRPK1 inhibitors reduce choroidal neovascularization in rodent models of exudative AMD, IOVS, 2013, 54(9), 6052-6062.
Grumati, et al., Autophagy is defective in collagen VI muscular dystrophies, and its reactivation rescues myofiber degeneration, Nature Medicine, 2010, 16, 1313-1320.
Gulbins, et al., Acid sphingomyelinase-ceramide system mediates effects of antidepressant drugs, Nature Medicine, 2013, 19, 934-938.
Hardisty, et al., Citalopram-Associated Central Retinal Vein Occlusion, Int. Ophthalmol., 2009, 29:303-304.
Jimenez-Sanchez, The Hedgehog signaling pathway regulates autophagy, Nature Communications, 2012, 3(1200), 1-11.
Kirkegaard, et al., Hsp70 stabilizes lysosomes and reverts Niemann-Pick disease-associated lysosomal pathology, Nature, 2010, 463(7280), 549-553.
Kolzer, et al., Interactions of acid sphingomyelinase and lipid bilayers in the presence of the tricyclic antidepressant desipramine, FEBS Letters, 2004, 559, 96-98.

(Continued)

*Primary Examiner* — Samira J Jean-Louis
(74) *Attorney, Agent, or Firm* — Quarles & Brady LLP

(57) ABSTRACT

A method of treating retinal diseases is disclosed that includes the step of administering an effective amount of a composition including an ASMase inhibitor to a retinal disease patient, wherein at least one disease symptom is either lessened or progression of the symptom is delayed.

10 Claims, 13 Drawing Sheets
(13 of 13 Drawing Sheet(s) Filed in Color)

(56) References Cited

OTHER PUBLICATIONS

Kornhuber, et al., Functional inhibitors of acid sphingomyelinase (FIASMAs): A novel pharmacological group of drugs with broad clinical applications, Cellular Physiology and Biochemistry, 2010, 26, 9-20.
Lajunen, et al., Topical drug delivery to retinal pigment epithelium with microfluidizer produced small liposomes, European Journal of Pharmaceutical Sciences, 2014, 62, 23-32.
Lakkaraju, et al., Low-density lipoprotein receptor-related protein mediates the endocytosis of anionic liposomes in neurons, Journal of Biological Chemistry, 2002, 277(17), 15085-15092.
Lakkaraju, et al., The lipofuscin fluorophore A2E perturbs cholesterol metabolism in retinal pigment epithelial cells, PNAS, 2007, 104(26), 11026-11031.
Le Guezennec, et al., Wip1-dependent regulation of autophagy, obesity, and atherosclerosis, Cell Metabolism, 2012, 16(1), 68-80.
Lee, et al., Acid sphingomyelinase modulates the autophagic process by controlling lysosomal biogenesis in Alzheimer's disease, JEM, 2014, 211(8), 1551-1570.
Nixon, The role of autophagy in neurodegenerative disease, Nature Medicine, 2013, 19, 983-997.
Pampliega, et al., Functional interaction between autophagy and ciliogenesis, Nature, 2013, 502, 194-200.
Penfold, et al., Modulation of major histocompatibility complex class II expression in retinas with age-related macular degeneration, Invest Ophthalmol Vis Sci, 1997, 38(10), 2125-2133.
Petersen, et al., Transformation-associated changes in sphingolipid metabolism sensitize cells to lysosomal cell death induced by inhibitors of acid sphingomyelinase, Cancer Cell, 2013, 24(3), 379-393.
Radu, et al, Bisretinoid-mediated complement activation on retinal pigment epithelial cells is dependent on complement factor H haplotype, Journal of Biological Chemistry, 2014, 289(13), 9113-9120.
Roth, et al., Potent and selective inhibitors of acid sphingomyelinase by bisphosphonates, Angewandte Chemie International Edition, 2009, 48, 7560-7563.
Rotstein, et al., Regulating Survival and Development in the Retina: Key Roles for Simple Sphingolipids, Journal of Lipid Research, 2010, 51:1247-1262.
Sander, 587: The Astemizole Retinopathy Trial: Effect of Astemizol on Diabetic Macular, Investigative Ophthalmology & Visual Science: Annual Meeting of the Association for Research in Vision and Ophthalmology, Association for Research in Vision and Ophthalmology, 2000, 41(4):S114.
Toops, et al., A detailed three-step protocol for live imaging of intracellular traffic in polarized primary porcine RPE monolayers, Experimental Eye Research, 2014, 124, 74-85.
Toops, et al., Cholesterol-mediated activation of acid sphingomyelinase disrupts autophagy in the retinal pigment epithelium, Molecular Biology of the Cell, 2015, 26(1), 1-14.
Travis, et al. Diseases caused by defects in the visual cycle: Retinoids as potential therapeutic agents, Annu. Rev. Pharmacol Toxicol, 2007, 47, 469-512.
Tunc, Maculopathy Following Extended Usage of Clomiphene Citrate, Eye, 2014, 28:1144-1146.
Wikipedia, The Free Encyclopedia, "FIASMA", Current Revision, Edited by Klbrain (talk / contribs), Aug. 2015.
Zhao, et al., mTOR-mediated dedifferentiation of the retinal pigment epithelium initiates photoreceptor degeneration in mice, J Clin Invest., 2011, 121(1), 369-383.
Zhou, et al., Complement activation by bisretinoid constituents of RPE lipofuscin, Invest Ophthalmol Vis Sci, 2009, 50(3), 1392-1399.
PCT International Search Report and Written Opinion, PCT/US2015/036982, dated Sep. 24, 2015.
Busik, J.V., W.J. Esselman, and G.E. Reid. 2012. Examining the role of lipid mediators in diabetic retinopathy. Clin Lipidol. 7:661-675.
Dannhausen, K., M. Karlstetter, A. Caramoy, C. Volz, H. Jagle, G. Liebisch, O. Utermohlen, and T. Langmann. 2015. Acid sphingomyelinase (aSMase) deficiency leads to abnormal microglia behavior and disturbed retinal function. Biochem Biophys Res Commun. 464:434-440.
Fan, J., B.X. Wu, and C.E. Crosson. 2016. Suppression of Acid Sphingomyelinase Protects the Retina from Ischemic Injury. Invest Ophthalmol Vis Sci. 57:4476-4484.
Feskanich, D., E. Cho, D.A. Schaumberg, G.A. Colditz, and S.E. Hankinson. 2008. Menopausal and reproductive factors and risk of age-related macular degeneration. Arch Ophthalmol. 126:519-524.
Fox, T.E., X. Han, S. Kelly, A.H. Merrill, 2nd, R.E. Martin, R.E. Anderson, T.W. Gardner, and M. Kester. 2006. Diabetes alters sphingolipid metabolism in the retina: a potential mechanism of cell death in diabetic retinopathy. Diabetes. 55:3573-3580.
Fraser-Bell, S., J. Wu, R. Klein, S.P. Azen, and R. Varma. 2006. Smoking, alcohol intake, estrogen use, and age-related macular degeneration in Latinos: the Los Angeles Latino Eye Study. Am J Ophthalmol. 141:79-87.
Frouws, M.A., B.G. Sibinga Mulder, E. Bastiaannet, M.M. Zanders, M.P. van Herk-Sukel, E.M. de Leede, B.A. Bonsing, J.S. Mieog, C.J. Van de Velde, and G.J. Liefers. 2017. No association between metformin use and survival in patients with pancreatic cancer: An observational cohort study. Medicine (Baltimore). 96:e6229.
Gandini, S., M. Puntoni, B.M. Heckman-Stoddard, B.K. Dunn, L. Ford, A. DeCensi, and E. Szabo. 2014. Metformin and cancer risk and mortality: a systematic review and meta-analysis taking into account biases and confounders. Cancer Prev Res (Phila). 7:867-885.
Klein, R., B.E. Klein, S.C. Jensen, K.J. Cruickshanks, K.E. Lee, L.G. Danforth, and S.C. Tomany. 2001. Medication use and the 5-year incidence of early age-related maculopathy: the Beaver Dam Eye Study. Arch Ophthalmol. 119:1354-1359.
Kornhuber, J., P. Tripal, M. Reichel, C. Muhle, C. Rhein, M. Muehlbacher, T.W. Groemer, and E. Gulbins. 2010. Functional Inhibitors of Acid Sphingomyelinase (FIASMAs): a novel pharmacological group of drugs with broad clinical applications. Cellular physiology and biochemistry : international journal of experimental cellular physiology, biochemistry, and pharmacology. 26:9-20.
Pikuleva, I.A., and C.A. Curcio. 2014. Cholesterol in the retina: The best is yet to come. Prog Retin Eye Res.
Suissa, S. 2012. Randomized Trials Built on Sand: Examples from COPD, Hormone Therapy, and Cancer. Rambam Maimonides Med J. 3:e0014.
Suissa, S., and L. Azoulay. 2012. Metformin and the risk of cancer: time-related biases in observational studies. Diabetes Care. 35:2665-2673.
Toops, K.A., L.X. Tan, Z. Jiang, R. Radu, and A. Lakkaraju. 2015. Cholesterol-mediated activation of acid sphingomyelinase disrupts autophagy in the retinal pigment epithelium. Mol Biol Cell. 26:1-14.
Wu, B.X., J. Fan, N.P. Boyer, Rim. Jenkins, Y. Koutalos, Y.A. Hannun, and C.E. Crosson. 2015. Lack of Acid Sphingomyelinase Induces Age-Related Retinal Degeneration. PLoS One. 10:e0133032.
Amsterdam, J.D., D.J. Brunswick, L. Potter, A. Winokur, and K. Rickels. 1985. Desipramine and 2-hydroxydesipramine plasma levels in endogenous depressed patients. Lack of correlation with therapeutic response. Archives of general psychiatry. 42:361-364.
Baumann, P., S. Ulrich, G. Eckermann, M. Gerlach, H.J. Kuss, G. Laux, B. Muller-Oerlinghausen, M.L. Rao, P. Riederer, G. Zernig, C. Hiemke, and g. Arbeitsgemeinschaft fur Neuropsychopharmakologie und Pharmakopsyhiatrie-Therapeutic Drug Monitoring. 2005. The AGNP-TDM Expert Group Consensus Guidelines: focus on therapeutic monitoring of antidepressants. Dialogues in clinical neuroscience. 7:231-247.
Tan, L.X., K.A. Toops, and A. Lakkaraju. 2016. Protective responses to sublytic complement in the retinal pigment epithelium. Proceedings of the National Academy of Sciences of the United States of America. 113:8789-8794.
Toops, K.A., L.X. Tan, Z. Jiang, R.A. Radu, and A. Lakkaraju. 2015. Cholesterol-mediated activation of acid sphingomyelinase

(56) References Cited

OTHER PUBLICATIONS disrupts autophagy in the retinal pigment epithelium. Molecular biology of the cell. 26:1-14.

* cited by examiner

USE OF INHIBITORS OF ACID SPHINGOMYELINASE TO TREAT ACQUIRED AND INHERITED RETINAL DEGENERATIONS

CROSS-REFERENCE TO RELATED APPLICATIONS

This application claims priority to U.S. Patent Ser. No. 62/015,753, filed Jun. 23, 2014, which is incorporated by reference herein.

STATEMENT REGARDING FEDERALLY SPONSORED RESEARCH OR DEVELOPMENT

This invention was not made with government support.

BACKGROUND

Over 30 million people currently suffer from AMD, the most common cause of permanent vision loss among older adults. There are currently no approved therapies for geographic atrophy, which affects 90% of AMD patients (Meleth et al., 2011), or for juvenile-onset macular degenerations like Stargardt disease, which has a prevalence of 1 in 8000 children (Haji Abdollahi and Hirose, 2013).

This lack of effective treatments is largely due to limited insight into disease mechanisms. Current clinical trials for AMD and Stargardt disease are focused on stem cell transplants or intravitreal injections of antibodies to complement pathway proteins (clinicaltrials.gov), all of which require periodic (monthly to quarterly) injections into the vitreous. This mode of administration has been widely used to administer VEGF antibodies to treat wet AMD. Intravitreal injections have numerous unacceptable consequences including endophthalmitis, retinal detachment and increased risk of developing geographic atrophy (Lois, et al., 2013).

"Wet" AMD, also known as choroidal neovascularization, is caused by abnormal growth of choroidal blood vessels into the retina. Antibodies to vascular endothelial growth factor (VEGF) are currently used to prevent blood vessel growth. The more chronic form of the disease is called "dry" AMD, or geographic atrophy, where progressive degeneration of the retinal pigment epithelium and subsequent loss of overlying photoreceptors leads to a slow decline in central, high-resolution vision. There are no approved therapies for dry AMD.

A large-scale multicenter trial on high dose antioxidant and carotenoid supplements recently showed that the supplements slow the progression of AMD from early to late stages but do not prevent disease onset. EMIXUSTAT, a visual cycle modulator that decreases the formation of A2E and lipofuscin is currently in Phase II trials. In Phase I trials, EMIXUSTAT caused a dose-dependent delay in dark adaptation and dyschromatopsia (Kubota et al., 2012), suggesting that this could potentially limit its use in chronic diseases like dry AMD.

Thus, there is a strong need for small molecule lipophilic drugs with good safety profiles that can be administered orally or as topical formulations to the eye to treat macular dystrophies. Unlike hydrophilic drugs, lipophilic drugs can reach the retina by easily crossing the outer blood-retinal barrier, which is formed by the tight junctions of the retinal pigment epithelium (RPE).

Retinal Disease Biology

The RPE, which sits beneath the photoreceptors in the retina, performs numerous functions critical for vision, including the daily phagocytosis and degradation of shed photoreceptor outer segments (Bok, 1993). The RPE is also the primary site of damage in many retinal degenerative diseases including AMD (Ambati and Fowler, 2012). The RPE is a post-mitotic tissue and with age, undigested outer segment components accumulate in the form of lipofuscin in RPE lysosomes. This lipofuscin is composed primarily of vitamin A metabolites called bisretinoids. A major component of RPE lipofuscin is A2E, which is a Schiff-base adduct of vitamin A and ethanolamine. Although increasing levels of lipofuscin and A2E are hallmarks of retinal degenerations including AMD, Stargardt and Best diseases (Rattner and Nathans, Nature Neuroscience, 2006 and Ambati and Fowler, supra), precisely how they harm the RPE and promote vision loss is unclear.

Our data has shown that lipofuscin and A2E increase lysosomal cholesterol in a primary RPE cell-based model that recapitulates key features of AMD (Lakkaraju et al., 2007) and in a mouse model of Stargardt disease (Toops et al., 2015). Cholesterol accumulation caused by lipofuscin and A2E interferes with multiple steps of autophagy, an essential mechanism for clearing debris in the post-mitotic RPE. High-speed live imaging showed that autophagosome biogenesis and trafficking is significantly disrupted in RPE with the bisretinoid A2E due to disrupted transport of autophagosomes.

In the present study, our data demonstrate a mechanism by which A2E-induced excess lysosomal cholesterol activates acid sphingomyelinase (ASMase), the enzyme that hydrolyzes sphingomyelin to ceramide. Ceramide promotes acetylation of tubulin on stabilized microtubules, leading to impaired trafficking of autophagosomes. We show that high ceramide levels are directly responsible for the autophagic block in RPE with A2E because treatment with the ASMase inhibitor desipramine (Kolzer et al., 2004), a tricyclic antidepressant, decreased tubulin acetylation, corrected trafficking defects and restored autophagic flux in the RPE. Moreover, we show that desipramine is very effective in reversing pro-inflammatory conditions in RPE with bisretinoids by (i) increasing CD59 delivery to the plasma membrane; (ii) increasing the efficiency of membrane repair after complement attack; (iii) limiting the production of reactive oxygen species; and (iv) decreasing MHC-II protein levels.

SUMMARY OF THE INVENTION

According to a first aspect, a method of treating retinal diseases includes the step of administering an effective amount of a composition comprising an ASMase inhibitor to a retinal disease patient. At least one of retinal disease symptom is lessened or progression of the symptom is delayed.

According to a second aspect, a method of treating macular degeneration in a subject in need thereof includes the steps of identifying a subject with macular degeneration and administering to the subject a therapeutically effective amount of a composition including an inhibitor of acid sphingomyelinase activity.

According to a third aspect, a method of treating macular degeneration in a subject in need thereof, includes the steps of identifying a subject with at least one of a) an accumulation of soft, large drusen, b) increased fundus autofluorescence, and c) delayed dark adaptation, and administering to the subject a therapeutically effective amount of a topical composition comprising desipramine a composition comprising an inhibitor of acid sphingomyelinase activity.

BRIEF DESCRIPTION OF THE DRAWINGS

This patent application file contains at least one drawing executed in color. Copies of this patent or patent application publication with color drawings will be provided by the Office upon request and payment of the necessary fee.

DETAILED DESCRIPTION OF THE INVENTION

Figures 1A, 1B, 1C, 1D, 1E, 1F, 1G:
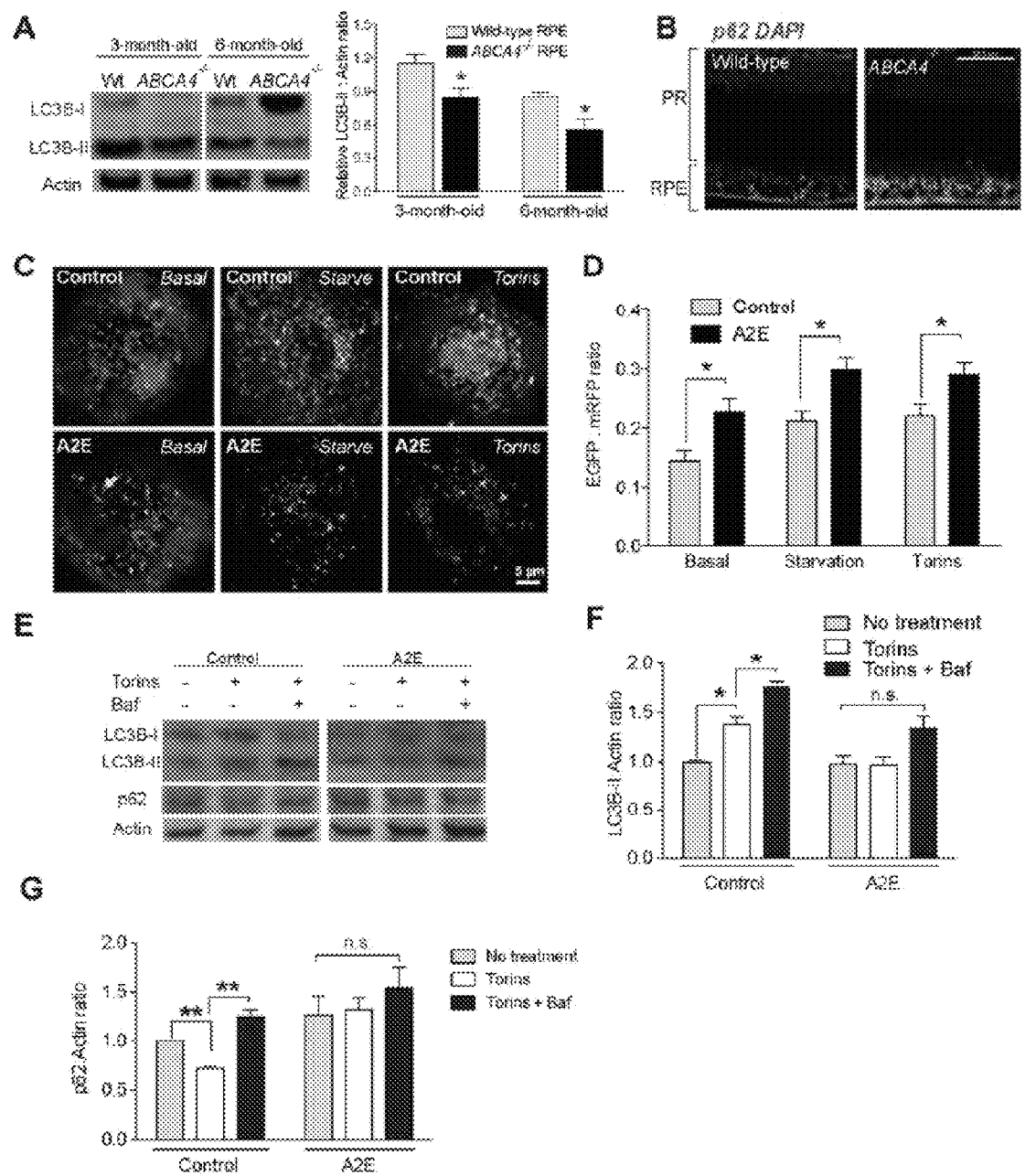
FIG. 1A-G. Regulation of autophagy in the RPE (A) Representative immunoblot and quantification of LC3B-II levels in the RPE of 3- and 6-month-old wild-type (grey bars) and ABCA4$^{-/-}$ (black bars) mice. Significantly less than age-matched wild-types, *, p<0.05, n≥9 animals per group. (B) Immunohistochemistry for p62 (green) in retinal cryosections from 6-month-old wild-type and ABCA4$^{-/-}$ mice. PR—photoreceptors; RPE—retinal pigment epithelium. Bar: 20 μm. (C) Stills from live imaging of tfLC3 in primary RPE to monitor basal autophagy and autophagic flux after mTOR inhibition by serum starvation or Torin1 and Torin 2 (both for 2 hours). (D) Quantification of EGFP/mRFP ratios of cells in (C). n=30 cells per condition. *, significantly greater than corresponding control cells, p<0.01. (E) Representative immunoblot of LC3B-I, LC3B-II and p62 protein levels in control or A2E-laden primary RPE monolayers untreated, or treated with Torins±Bafilomycin A1 (Baf, 100 nM for 2 hours). (F) Quantification of LC3B-II immunoblots, n≥9 per condition; *, p<0.01; n.s.—not significant. (G) Quantification of p62 immunoblots, n≥9 per condition; **, p<0.001; n.s.—not significant.

We have identified a stepwise mechanism by which excess lysosomal cholesterol traps a lipid called bis(monoacyl-glycero)phosphate (BMP) within lysosomes. BMP is an activator of ASMase activity and the resulting increase in ceramide levels interfere with autophagosome biogenesis, autophagosome traffic and fusion with lysosomes. Declining autophagy with age has emerged as a key pathogenic factor in Alzheimer's and Parkinson's diseases, and could also contribute to RPE dysfunction as a precursor to permanent vision loss.

This finding suggests to us that inhibition of ASMase is a therapeutic target in retinal dystrophies associated with lipofuscin accumulation. Thus, tricyclic antidepressants and other ASMase inhibitors constitute a new line of therapy for AMD and for inherited retinal diseases characterized by abnormal accumulation of lipofuscin.

After we made the connection between ASMase inhibition and retinal disease treatment, we examined two epidemiological studies, the Beaver Dam Eye Study based at UW (Klein et al., 2001) and a pooled study from three continents (van Leeuwen et al., 2004), which indicate that use of tricyclic antidepressants (TCA) is associated with a decreased risk of developing early AMD. While these initial studies on TCA use in AMD were published over a decade ago, they did not address the mechanism underlying the protective effect (Klein et al., 2001; van Leeuwen et al., 2004). These studies had no baseline data on dosage and duration of medication use, and both one-time users and chronic users of TCAs were grouped together.

In summary, ASMase inhibitors are effective for both preventing and treating macular dystrophies because (i) our data show that a short 3 hour incubation with desipramine, sertraline or astemizole completely reversed the autophagic block induced by A2E; (ii) other ASMase inhibitors amitriptyline, fluoxetine and zoledronic acid decreased acetylated tubulin levels in RPE with A2E back to control levels; (iii) Desipramine maintained RPE integrity and prevented mitochondrial oxidative damage after complement attack; (iv) ASMase inhibitors are low molecular weight, lipophilic drugs that are well-absorbed after oral administration and are blood-brain barrier permeable, which makes it likely that they will be permeable to the RPE outer blood-retinal barrier and the corneal barrier after topical administration; and (v) these drugs are all FDA approved and have well-established safety and efficacy profiles.

Diseases Treated by the Present Invention

In one embodiment, the present invention is a method of treating retinal diseases comprising the steps of administering an effective amount of a composition comprising an ASMase inhibitor to a retinal disease patient, wherein disease symptoms are lessened.

Preferred diseases for treatment by the present invention include age-related macular degeneration (AMD), Stargardt macular dystrophies (autosomal dominant and autosomal recessive forms), Best vitelliform macular dystrophy and neuronal ceroid lipofuscinoses (NCLs), such as Batten's Disease. These diseases are all associated with an abnormal accumulation of lipofuscin, a complex mixture of visual cycle retinoids, in the retinal pigment epithelium (RPE) (Travis et al., 2007).

The method is suitable for emerging disease states. If a patient is deemed at risk of developing early AMD by their ophthalmologist after a fundus exam, the patient could likely be a candidate for treatment. One would most likely start treatment when the exam reveals presence of soft, large drusen, which are confirmed risk factors for AMD. Treatment is suitable for any age/gender.

ASMase Inhibitors of the Present Invention

The present invention includes the use of an acid sphingomyelinase (ASMase) inhibitor for the treatment of acquired and inherited retinal diseases. In our studies described below, we tested inhibitors of ASMase (Kolzer et al., 2004), and desipramine (a functional inhibitor) is a preferred ASMase of the present invention. Desipramine is also known as desmethylimipramine. Brand names are NORPRAMIN and PERTOFRANE. Desipramine is the active metabolite of imipramine (also known as melipramine and sold under the brand name TOFRANIL).

We envision that other ASMase inhibitors would be suitable. A number of low molecular weight cationic lipophilic drugs that are currently approved by the FDA and are on the market are known to inhibit ASMase function (see Table 1 of Kornhuber et al., 2010, incorporated by reference). These drugs are all orally bioavailable and have established safety and efficacy profiles.

We envision that these drugs will be suitable topically as well as orally. The best orally bioavailable drugs are small molecular weight, lipophilic compounds which are also ideal characteristics for topical eye formulations.

Additionally, we envision that drugs that are known to structurally inhibit ASMase (e.g., bisphosphonates like zoledronic acid (Roth et al., 2009)) would be suitable.

We further envision that additional dibenzazepine derivatives aside from desipramine may be suitable.

Preferred Methods of Delivery of Acid Sphingomyelinase Inhibitors to the Retinal Pigment Epithelium We envision that acid sphingomyelinase inhibitors will be delivered orally (either single drugs or in combination), topically or via sustained release scleral implants.

Applicants envision that the treatment method of the present invention may be of different modalities. For example, one may wish to deliver the ASMase inhibitor orally, intravenously, intravitreal injections, topical, transmucosal (nasal, buccal/sublingual, vaginal, ocular and rectal) and inhalation routes. Note that topical delivery directly to the eye may be via an ocular route, which can be transmucosal because the drug is thought to go through the mucous membrane of the conjunctiva. We also envision that the drug may be delivered through corneal drug delivery, which is not transmucosal.

In one version of the invention, the drug is delivered orally. Generic oral dosages used in patients currently are 10-25 mg/day NORPRAMIN (desipramine) and 50-100 mg/day tofranil (imipramine).

In preferred embodiments of the present invention, we envision to following preferred formulations for topical drug delivery:

1. Eye Drop Solutions

Many of the acid sphingomyelinase inhibitors we have disclosed conform to the Lipinski rule of five (Leeson, Nature 2012), which are the five physicochemical features that predict oral bioavailability of the drug such as pKa, mol wt, lipophilicity, etc. One would preferably administer these drugs using eye drops. For example, drugs may be dissolved in sterile-filtered aqueous-based solutions containing 1% hydroxypropyl methylcellulose, 0.2% tyloxapol, 3.4% dextrose, 0.006% benzalkonium chloride, and 0.025% ethylenediaminetetraacetic acid (280 mOsm, pH 5.4), which has been shown to deliver small molecular weight compounds to the retina, RPE and choroid (Doukas et al., J Cell Physiol, 2008; Gammons et al., IOVS 2013)

2. Liposomes

Drugs may be encapsulated in liposomes and subjected to microfluidization, which decreases liposome size to <60 nm. Liposomes of this size administered topically (directly to the eye) can reach the RPE (Lajunen et al., 2014). Liposomes may be composed of phospholipids such as phosphatidylcholine, phosphatidylserine phosphatidylethanolamine and coated with polyethylene glycol to increase tissue stability. Preferably, liposomes will be actively targeted to the RPE using either the transferrin receptor (Lajunen et al., 2014) or the low-density lipoprotein-related receptor protein (LRP) (Lakkaraju et al., 2002).

3. Gels and Ointments

In one embodiment of the invention, the inhibitor is delivered in a gel or ointment delivered directly to the eye. For example, drugs may be loaded in bases such as CARBOPOL 934 or liquid paraffin listed in the US Pharmacopoeia.

Representative Dosages and Dosage Schedules

If one were to apply the medication as a topical application, we envision that the dose would be applied daily or every other day until efficacy is established. Currently, we use 2.6 μg/ml in vitro. Assuming 95% of topically applied dose doesn't reach target (usual case with eye formulations), we envision starting at 0.1 mg and going up to 1 mg per dose.

If one were to use an oral administration, doses will be based on published data for the inhibitor (Gulbins et al., Nature Medicine, 2013 and Petersen et al., Cancer Cell, 2013). Generic oral dosages used in patients currently: 10-25 mg/day norpramin (desipramine); 50-100 mg/day tofranil (imipramine). We envision that a preferred oral dose range will be between 10-100 mg/day.

Evaluating Effective Drug Delivery

After the treatment of the present invention, one will wish to evaluate the efficacy of the treatment. In one embodiment, one may evaluate the progression of the disease. In one embodiment, a successful treatment would result in lack or slowing of disease progression. For example, for an AMD patient, one would wish to evaluate the progression of the following disease symptoms: accumulation of soft, large drusen; increased fundus autofluorescence; delayed dark adaptation.

If one were evaluating the treatment from a molecular level (for example, with a disease model), one may wish to examine: 1) Quantification of ceramide levels and acid sphingomyelinase activities in the RPE after topical and oral administration in mice using mass spectrometry; and 2) Measurement of autophagic flux in the RPE in wild-type and Stargardt disease mice.

EXAMPLES

Example 1. Cholesterol-Mediated Activation of Acid Sphingomyelinase Disrupts Autophagy in the Retinal Pigment Epithelium Macroautophagy (hereafter referred to as autophagy) is a bulk degradative pathway where double-membraned structures called autophagosomes enclose damaged proteins and organelles. Fusion of autophagosomes with the endo-lysosomal system delivers hydrolytic enzymes required to degrade the sequestered cytosolic components (Rubinsztein et al., 2007; Choi et al., 2013). Formation of the autophagosome is initiated by the activation of autophagy-related (Atg) proteins in a hierarchical manner. The molecular machinery of autophagy is highly conserved and primarily regulated by the mammalian target of rapamycin (mTOR), in response to the nutrient and metabolic status of the cell. Autophagy occurs at a basal level in most cells and is increased under conditions of stress, when it promotes survival by repurposing degraded material to support metabolism within the cell (Codogno et al., 2012).

Inefficient autophagy has been implicated in the pathogenesis of neurodegenerative diseases because post-mitotic neurons are especially susceptible to the accumulation of defective organelles and protein aggregates (Nixon, 2013). Autophagy is also critical for maintaining the health of the neural retina: in aged mice or mice with retina-specific deletions of Atg5, decreased autophagic flux precedes photoreceptor degeneration (Rodriguez-Muela et al., 2013) and autophagy induction preserves differentiation of the retinal pigment epithelium (RPE) and prevents photoreceptor death after oxidative stress (Zhao et al., 2011) or exposure to Fas ligand (Besirli et al., 2011). In the post-mitotic RPE, which nourishes and supports the overlying photoreceptors, autophagy is increased in response to diverse stressors including exposure to intense light, oxidative stress, mitochondrial poisons, cigarette smoke and cell swelling (Reme et al., 1999; Kunchithapautham and Rohrer, 2007a, b; Chen et al., 2013; Doyle et al., 2014; Wang et al., 2014).

A key function performed by the RPE critical for photoreceptor health is the circadian phagocytosis and lysosomal degradation of shed photoreceptor outer segment (OS) tips (Bok, 1993). Each RPE cell contacts 30-50 photoreceptors, which shed about 10% of their OS length daily. Over a lifetime, this immense metabolic activity results in the progressive accumulation of undigested OS components called lipofuscin in RPE lysosomes (Sparrow et al., 2012). RPE lipofuscin differs from that in other post-mitotic tissues in that it is primarily composed of bisretinoid metabolites of vitamin A, generated as by-products of the visual cycle (Eldred and Lasky, 1993). Light induces isomerization of the visual chromophore 11-cis-retinal (11CR) to all-trans-retinal (ATR), which is flipped by the ATP binding cassette transporter A4 (ABCA4) from the lumen to the cytosolic side of the disc membrane and reduced to non-toxic all-trans-retinol by retinol dehydrogenase 8 (Weng et al., 1999). Delayed removal of 11CR and ATR from disc membranes makes them susceptible to condensation reactions that ultimately result in the formation of vitamin A derivatives such as the lipofuscin bisretinoid A2E in RPE lysosomes (Sparrow et al., 2012). Once formed, lipofuscin bisretinoids remain in the RPE for life because their unique structures render them resistant to lysosomal degradation.

Chronic accumulation of these bisretinoids has been implicated in the pathology of numerous blinding retinal diseases including Stargardt disease, Best disease and age-related macular degeneration (AMD) (Ambati and Fowler, 2012; Sparrow et al., 2012). We previously demonstrated that A2E, a cone-shaped lipid, displaces cholesterol from lipid bilayers and sequesters cholesterol in RPE late endosomes and lysosomes (Lakkaraju et al., 2007). Since membrane cholesterol levels modulate autophagosome-lysosome interactions (Fraldi et al., 2010; Koga et al., 2010; Sarkar et al., 2013), we hypothesized that cholesterol storage induced by lipofuscin bisretinoids would inhibit autophagic clearance in the RPE. OS phagocytosis has been shown to recruit autophagic machinery in the RPE (Kim et al., 2013; Frost et al., 2014; Yao et al., 2014) and inefficient autophagy is thought to play a part in the pathogenesis of retinal diseases such as AMD (Bowes Rickman et al., 2013; Frost et al., 2014). However, how innate processes such as progressive accumulation of lipofuscin bisretinoids impact autophagy in the RPE is not well understood.

Here, we report decreased autophagosome biogenesis and autophagic flux in the RPE of ABCA4$^{-/-}$ disease mice, which have high levels of A2E and other bisretinoids (Radu et al., 2011). High-speed live imaging of primary RPE by spinning disk confocal microscopy (Toops et al., 2014) showed that A2E interfered with autophagosome biogenesis, constrained autophagosome traffic and decreased autophagic flux. Our data unveil a step-wise molecular mechanism by which lipofuscin- and A2E-induced lysosomal cholesterol storage (Lakkaraju et al., 2007) activates acid sphingomyelinase (ASMase) by sequestering the anionic lipid bis (monoacyl-glycero)phosphate (BMP), an ASMase co-factor (Kirkegaard et al., 2010). The resulting increase in ceramide levels lead to increased tubulin acetylation (He et al., 2012; He et al., 2014). Our data show that bidirectional motility of autophagosomes and autophagosome-lysosome fusion are impaired in cells with acetylated microtubules. In support of a central role for cholesterol-mediated ASMase activation in regulating autophagy, we demonstrate that a drug that promotes cholesterol efflux (Lakkaraju et al., 2007) and an US Food and Drug Administration (FDA)-approved ASMase inhibitor (Kornhuber et al., 2010) restore efficient autophagosome transport and autophagic flux in the RPE.

There are two significant implications of our study: first, our data show that autophagy in the RPE is regulated in response to the immense metabolic demands placed on the cell, adding to a growing body of evidence for specialized regulation of autophagy based on tissue, function and context (Grumati et al., 2010; Jimenez-Sanchez et al., 2012; Le Guezennec et al., 2012; Pampliega et al., 2013). Second, our studies suggest that ASMase inhibition could be a potential novel therapeutic strategy not only in macular degenerations associated with excess lipofuscin accumulation but also in diseases characterized by abnormal cholesterol homeostasis and impaired autophagy (Le Guezennec et al., 2012; Nixon, 2013; Barmada et al., 2014; Lee et al., 2014).

Materials and Methods

Cells

Primary RPE were harvested from freshly enucleated porcine eyes (Hart and Vold, Baraboo, Wis.) as described (Toops et al., 2014): briefly, the anterior segment was removed at the ora serrata and the retina was gently detached by clipping at the optic nerve head. RPE cells were isolated from eyecups upon incubation with 0.5% trypsin with 5.3 mM EDTA in HBSS and plated onto T25 flasks in DMEM with 1% heat-inactivated fetal bovine serum (FBS, ATCC). To generate polarized cultures, cells were plated at confluence (~300,000 cells/cm$^2$) onto collagen-coated TRANSWELL (Corning) semi-permeable membrane filters. After two weeks, monolayers had trans-epithelial electrical resistances of >300 ohm·cm$^2$, localized Na$^+$, K$^+$-ATPase apically, expressed tight junction proteins (e.g., ZO-1) and RPE differentiation markers (e.g., RPE65) (Toops et al., 2014).

Animals

Wild-type and ABCA4$^{-/-}$ mice (both 129/Sv strain on Rpe65 Leu450 background) were raised under a 12-h cyclic light and fed a standard rodent diet (NIH-31, 7013 Harlan Teklad, Madison, Wis.). Mouse studies were done in adherence to guidelines established by the UCLA Animal Research Committee and The Association for Research in Vision and Ophthalmology statement for the Use of Animals in Ophthalmic and Vision Research. Animals were euthanized ~4-6 h after light onset, eyes were removed and hemisected. The anterior portion containing the cornea, lens, and vitreous was discarded. Eyecups containing retina, RPE, choroid, and sclera were frozen in liquid N$_2$ and stored at −80° C. for further processing (Radu et al., 2011).

Immunoblotting

RPE harvested from mouse eyecups were sonicated in lysis buffer with protease inhibitors for 10 min. Primary RPE on TRANSWELL filters were harvested and lysed with NE-PER nuclear and cytoplasmic extraction reagents (Thermo Scientific #78833) according to the manufacturer's recommendation. Protein concentrations were measured with DC assay (BioRad). Samples (20 µg/lane) were resolved in 4-12% NUPAGE Bis-Tris Precast Gels (INVITROGEN) at 130V. Proteins were then transferred onto nitrocellulose membrane using IBLOT dry transfer system (INVITROGEN), blocked in 5% milk in TBS-T for 1 hour before incubating in primary antibody overnight at 4° C. Membranes were probed with antibodies to LC3B (1:3000, Novus NB600-1384 for pig and 1:500, Sigma L7543 for mouse), p62/SQSTM1 (1:1000, ARP03-GP62-C) and actin (1:5000, Santa Cruz) followed by horseradish peroxidase-conjugated secondary antibodies. Immunoblots were visualized by ECL substrate (Thermo Scientific) and quantified using Image Studio (LI-COR).

Pharmacological Treatments

The lipofuscin bisretinoid A2E was synthesized according to published protocols and purified by HPLC (>97%, ESI-MS) (Lakkaraju et al., 2007). RPE were exposed to either a chronic low-dose of A2E (50 nM for 3 weeks) or an acute high-dose of A2E (10 µM for 6 h, followed by a 48 h chase). Quantification of A2E levels in cells was performed by HPLC as previously reported (Radu et al., 2011). Other drugs used were the mTOR inhibitors Torin 1 and Torin 2 (50 nM and 1.5 µM, respectively, for 2 h, TOCRIS), the vacuolar ATPase inhibitor bafilomycin A1 (100 nM for 2 h, EMD Millipore), the LXRα agonist TO901317 (1 µM for 20 h, Cayman Chemicals), the HDAC6 inhibitor trichostatin A (TSA, 500 nM, 16 h, Sigma) and the ASMase inhibitor desipramine (10 µM for 3 h, Sigma). To depolymerize MTs, cells were treated with 33 µM nocodazole for 30 minutes, followed by cold-treatment (4° C.) for 30 minutes (Kreitzer et al., 2003). At the concentrations and exposure times used, none of these drugs caused alterations in RPE cell morphology or physiology (monitored by TER measurements, ZO-1 and organelle marker staining).

Immunofluorescence Staining and Quantification

Filter-grown cells were fixed in 2% paraformaldehyde for 10 min, blocked in 1% BSA in PBS and incubated with specific primary antibodies for 1 hour: mouse monoclonal anti-acetylated tubulin clone 6-11B-1 (1:1000, Sigma), rat monoclonal anti-tyrosinated α-tubulin (1:200, Santa Cruz), mouse anti-LBPA (1:500, Echelon Z-LBPA), mouse anti-ceramide (1:10, Enzo) and rat anti-Z0-1 1:3000 (Xu et al., 2012). ALEXAFLUOR secondary antibodies were used at 1:500 and rhodamine-phalloidin (Cytoskeleton, PHDR1) at 1:200. Filters were mounted under coverslips on glass slides under VECTASHIELD (Vector labs), sealed and visualized with Andor Revolution XD spinning disk confocal microscope using a 60×1.4 NA oil objective with identical exposures and gains for each antibody. Acetylated tubulin-labeled stable microtubules (≥5 µm in length) after nocodazole treatment were analyzed manually in the Surpass mode of Imaris (Bitplane).

Immunohistochemistry

Cryosections of wild-type and ABCA4$^{-/-}$ mice retinas were blocked in PBS with 4% BSA and incubated with primary antibodies (diluted 1:100 in PBS with 4% BSA) for 48 h at 4° C. in a humidified chamber. Slides were rinsed to remove unbound antibodies and incubated with Alexa-conjugated secondary antibodies (1:500 in PBS with 4% BSA) for 18 h at 4° C. in a humidified chamber protected from light. Sections were rinsed, stained with DAPI for 5 min, rinsed and sealed under coverslips using VECTASHIELD as a mounting medium. Slides were imaged with the Andor Revolution XD spinning disk confocal microscope using a 40×1.4 NA oil objective with identical exposures and gains for each antibody.

Transfections

RPE cells were transfected with EGFP-LC3 or tandem fluorescent mRFP-GFP-LC3 (Addgene) using the AMAXA NUCLEOFECTOR II (Lonza). Approximately 1.5 million cells and 5 µg of plasmid DNA were used for each transfection. Cells were plated either on serum-coated glass-bottom dishes (Mattek) or TRANSWELL filters at confluence.

Spinning Disk Microscopy

Live imaging of autophagosome traffic and autophagic flux were performed on the Revolution XD spinning disk microscopy system (Andor) equipped with the Yokogawa CSU-X1 confocal spinning disk head, Nikon Eclipse Ti inverted microscope surrounded by an Okolab cage incubator, iXon x3 897 EM-CCD camera, Andor laser combiner with four solid state lasers at 405, 488, 561, and 640 nm and corresponding band-pass filter sets (Sutter), and ASI motorized stage with piezo-Z for rapid Z-stack acquisition. Andor IQ2 software was used for image acquisition and Imaris x64 (Bitplane) for image analysis. For live imaging, cells were serum starved for 2 h to induce autophagy and rapid z-stacks were acquired using the 100×1.49 NA Apo TIRF objective (Nikon) for ~50 frames at 37° C. Trafficking data was collected from three separate transfections for a total of at least 12-30 movies captured for treatment. During image acquisition care was taken to maintain the same laser power, exposure and electron-multiplying gain settings. Trafficking analysis was carried out using the Spots and Tracks modules of the Imaris software (Liu et al., 2010). After background subtraction (using the background subtraction algorithm and identical automatic threshold for all images) and smoothing (Gaussian algorithm with identical threshold settings for all images), Spots and Tracks algorithms were used to identify vesicles and follow them through time and cell-space to obtain total track length and track displacement. Statistical analysis of these data sets was performed using Excel (Microsoft) and PRISM (GraphPad).

Biochemical Assays

Cells were harvested by trypsinization and cell pellets were washed with PBS to remove residual medium. Cells were lysed in HNTG lysis buffer (50 mM Hepes, pH 7.4, 150 mM NaCl, 10% glycerol, 1.5 mM $MgCl_2$, 1% triton X-100) supplemented with protease inhibitors. Total protein was measured using the DC protein assay kit (BioRad). Cellular cholesterol was quantified using the Amplex Red cholesterol assay kit (INVITROGEN) as detailed previously (Lakkaraju et al., 2007). Single eyecups from wild-type and $ABCA4^{-/-}$ mice were homogenized in 50 µl of lysis buffer and processed as above. For measuring acid sphingomyelinase activity, cells were lysed in acidic pH and assays were performed using the sphingomyelinase fluorimetric assay kit from Cayman Chemicals according to the manufacturer's protocol.

Statistical Analysis

Data were analyzed using either a two-tailed t-test or one-way ANOVA followed by Bonferroni or Dunnett's post-tests (GraphPad PRISM). Unless otherwise stated, data are presented as Mean±S.E.M. of ≥3 independent experiments, with 3 to 4 replicates per condition per experiment. To analyze EGFP-LC3 trafficking data, Boolean gating was used to segment three regions (denoted by R1, R2 and R3 on the track displacement versus total track length graphs). Regions were defined by: minimum or maximum track length, minimum or maximum displacement and a slope of 0.5 (displacement divided by length). Tracks with slope <0.5 were taken as less straight (region 2) than those with slope of >0.5 (region 3). Tracks within each region are represented as a percent of total number of tracks in Tables 1 and 2. One-way ANOVA or t-tests were used to compare regions between treatment groups.

Results

Lipofuscin Bisretinoids Interfere with Canonical Autophagy in the RPE

To investigate whether lipofuscin bisretinoids impact autophagy in vivo, we measured microtubule-associated light chain 3B-II (LC3B-II) and p62/SQSTM1 levels in RPE of $ABCA4^{-/-}$ mice, which have high levels of lipofuscin bisretinoids such as A2E (Radu et al., 2011). Conversion of LC3B-I to its lipidated form (LC3B-II) is an indicator of autophagosome biogenesis and p62 levels are a measure of autophagic flux (Klionsky et al., 2012). $ABCA4^{-/-}$ RPE had significantly less LC3B-II (FIG. 1A) and more p62 (FIG. 1B) compared to RPE from age-matched wild-type mice, supporting the hypothesis that accumulation of lipofuscin bisretinoids is associated with defective autophagy in vivo. To determine how lipofuscin bisretinoids inhibit autophagy in the RPE, we established an in vitro model by exposing polarized porcine primary RPE monolayers (Toops et al., 2014) to the bisretinoid A2E, chronically (50 nM over three weeks) or acutely (10 µM for 6 h), either of which result in intracellular A2E levels comparable to those seen in the RPE of $ABCA4^{-/-}$ mice and in human Stargardt disease patients (Table 1).

TABLE 1

A2E levels in polarized primary pig RPE, mouse models and humans

| Model | Details | pmoles A2E per 100,000 RPE (mean ± SD) | ng A2E per 100,000 RPE (mean ± SD) | Notes |
|---|---|---|---|---|
| Primary pig RPE | No A2E control | Not detectable | — | Toops et al. |
| | 15 nM, 3 weeks | 4.92 ± 1.44 | 2.91 ± 0.85 | |
| | 50 nM, 3 weeks | 14.13 ± 2.71 | 8.37 ± 1.61 | |
| | 10 µM A2E, 6 h | 22.32 ± 0.23 | 13.21 ± 0.14 | |
| Wild-type mice | 3 months old | 1.58 ± 0.34 | 0.93 ± 0.20 | (Radu et al., 2011) |
| | 6 months old | 3.32 ± 0.01 | 1.96 ± 0.006 | |
| | 12 months old | 9.30 ± 1.80 | 5.51 ± 1.06 | |
| $Abca4^{-/-}$ mice | 3 months old | 8.37 ± 0.54 | 4.96 ± 0.32 | (Radu et al., 2011) |
| | 6 months old | 23.32 ± 2.47 | 13.81 ± 1.46 | |
| | 12 months old | 28.30 ± 5.80 | 16.75 ± 3.45 | |
| Normal human RPE | Seven normal subjects | 5.30 ± 2.98* | 3.14 ± 1.76 | * per 0.25 $cm^2$ (Mata et al., 2000) |
| Stargardt's human RPE | STGD1 #1 | 33* | 19.54 | * per 0.25 $cm^2$ |
| | STGD1 #2 | 61* | 36.11 | (Mata et al., 2000) |
| Aging human RPE (normal) | Ten subjects, 58-79 years | 145.27 ± 54.17 | 86 ± 32.1 | (Sparrow et al., 1999) |

In polarized primary RPE cells, autophagy was upregulated after mTOR inhibition, either by nutrient deprivation or treatment with the selective mTOR inhibitors Torin 1 and Torin 2. We used tandem fluorescent mRFP-GFP-LC3 (tfLC3) to monitor autophagy in primary RPE cells in real time. Upon fusion of autophagosomes with lysosomes, EGFP fluorescence is quenched in the acidic lysosomal pH and only the pH-insensitive mRFP signal is visible; therefore, ratios of EGFP to mRFP are a measure of autophagic flux (Klionsky et al., 2012). TfLC3 imaging showed significantly more EGFP puncta in cells treated with A2E compared to control cells, both at the basal level and after mTOR inhibition either by nutrient deprivation or Torin treatment (FIGS. 1C, 1D).

Figure 2:
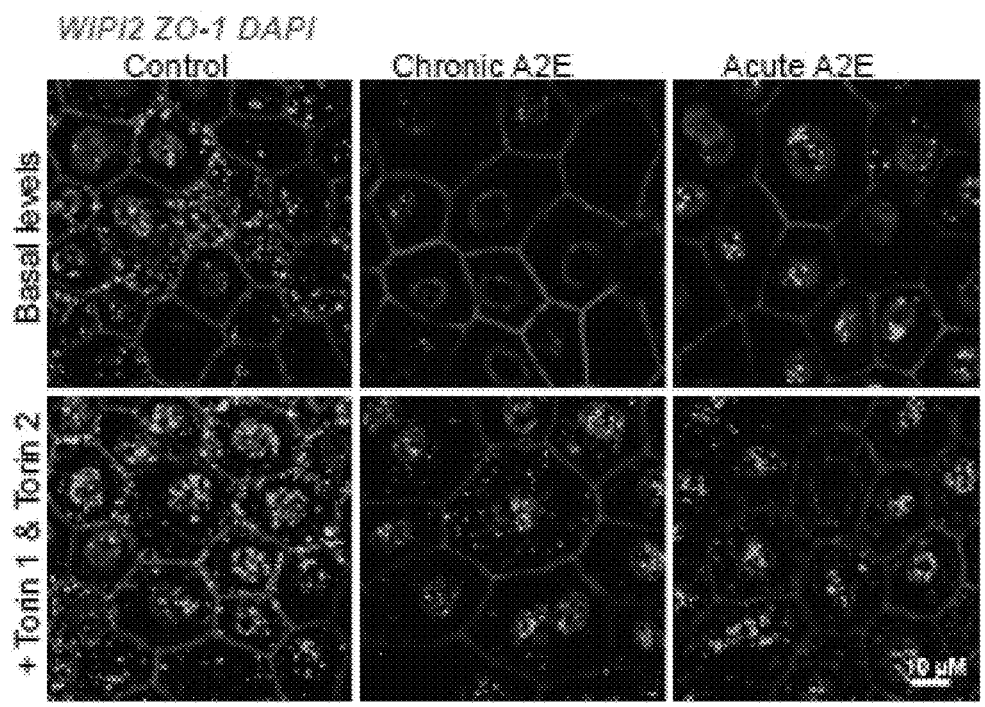
FIG. 2. Autophagosome biogenesis in the RPE. Immunofluorescence staining for WIPI2 (green), ZO-1 (red) and DAPI (blue) in control RPE or exposed to A2E as indicated, all treated with Torin 1 (50 nM) and Torin 2 (1.5 μM) for 2 h.

Immunoblotting of polarized primary RPE monolayers after mTOR inhibition showed significantly lower LC3B-II levels in cells treated with A2E compared to control RPE. The vacuolar ATPase inhibitor Bafilomycin A1, which prevents lysosomal degradation of LC3B, increased LC3B-II after mTOR inhibition in control cells but not cells exposed to A2E (FIGS. 1E, 1F). To confirm that A2E decreased autophagosome biogenesis, we immunostained primary RPE monolayers for WD repeat domain, phosphoinositide interacting 2 (WIPI2)-positive preautophagosomal structures (Polson et al., 2010). There were fewer WIPI2-labeled nascent autophagosomes at the basal state and after mTOR inhibition in cells with A2E, compared to control cells (FIG. 2). Immunoblotting also showed that there was significantly more p62 in cells with A2E after Torin treatment (FIGS. 1E, 1G), indicating a block in autophagic flux. Taken together, these data suggest that lipofuscin bisretinoids interfere with canonical autophagy in vivo in the ABCA4$^{-/-}$ mice and in primary RPE cells in culture.

Autophagosome Trafficking is Disrupted in RPE with the Bisretinoid A2E

Figures 3A, 3B, 3C, 3D, 3E:
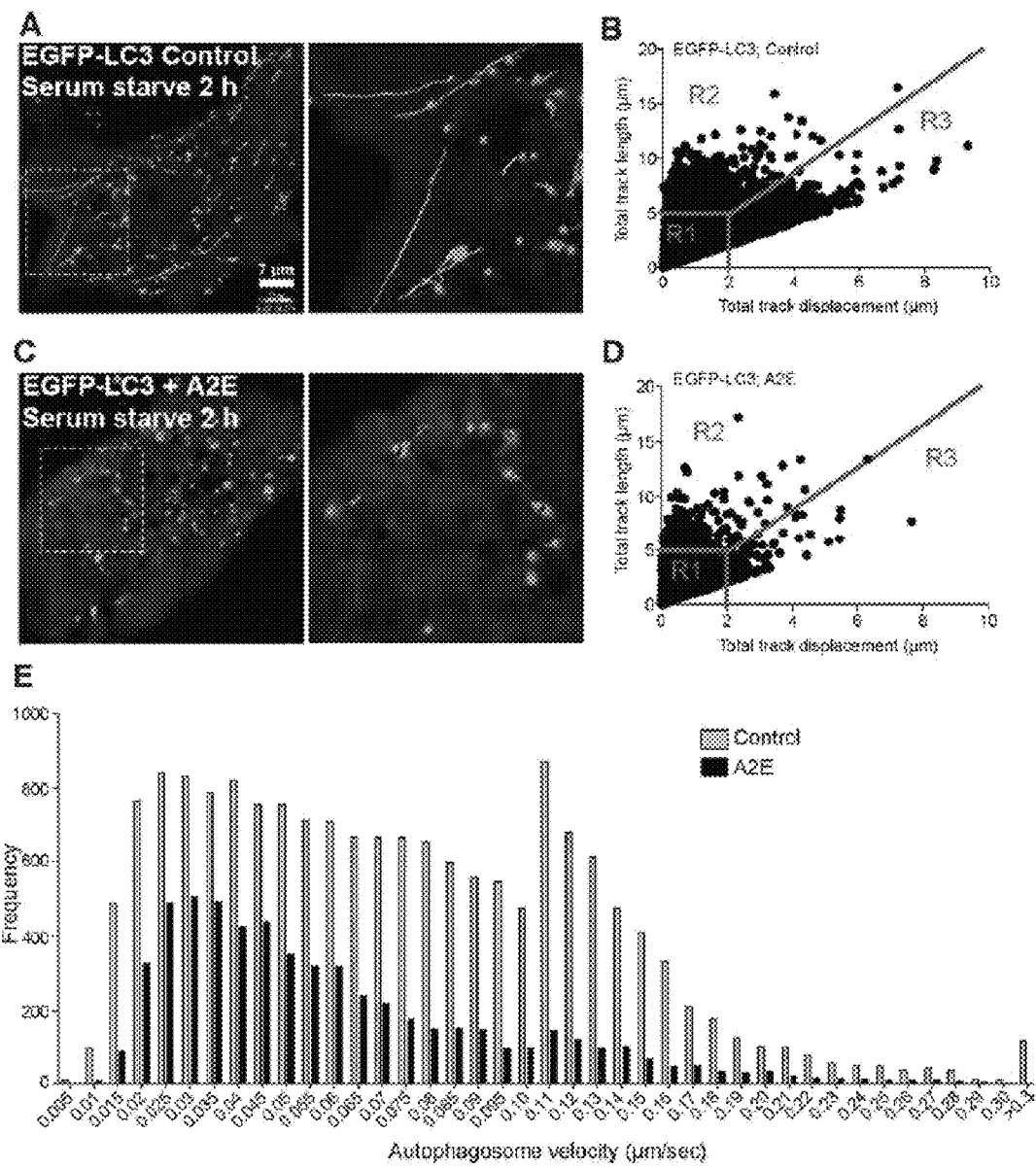
FIG. 3A-E. Live imaging of autophagosome trafficking in the RPE. (A) & (C) Stills from live imaging of EGFP-LC3 with spots and tracks superimposed in serum-starved RPE (A) untreated (control) or (C) exposed to A2E. Right panels—high-magnification images of areas denoted by white boxes in the left panels. (B) & (D) Plots of track displacement of EGFP-LC3-labeled autophagosomes versus total track length in untreated cells (B) or cells exposed to A2E (D). Boolean gating was used to analyze data as explained in the Methods. See Table 2 for R1, R2 and R3 percentages. (E) Frequency histogram of EGFP-LC3 labeled autophagosome velocities (μm/sec). Grey bars—control cells; black bars—cells treated with A2E.

Since tfLC3 imaging and p62 immunoblotting data showed a block in autophagosome-lysosome fusion and decreased autophagic flux in RPE with bisretinoids, we asked whether A2E interfered with the trafficking of autophagosomes. We performed live imaging of EGFP-LC3-labeled autophagosomes in untreated or A2E-laden primary RPE cells using high-speed spinning disk confocal microscopy. After serum starvation to induce autophagy, RPE with A2E had fewer EGFP-LC3 motile tracks compared to control cells (FIGS. 3A, 3C). We used 4D image analysis (Imaris, Bitplane) to quantify changes in autophagosome trajectories induced by A2E. To examine the efficiency of autophagosome transport, Spots and Tracks algorithms in Imaris were used to calculate how far each autophagosome traveled (track displacement length) as a function of the movement required to travel that distance (total track length) (Liu et al., 2010). Analysis of track displacement data by Boolean gating showed a significant decrease in the population of autophagosomes with long-range, directed movements (large displacement with long track lengths) in cells with A2E (FIGS. 3B, 3D and Table 2). Compared to control cells, RPE with A2E had fewer motile autophagosomes (aggregate number of motile tracks was 17,010 in control cells and 5,914 in cells with A2E), which moved with significantly lower velocities (FIG. 3E). How could A2E, which is present in RPE late endosomes and lysosomes (Lakkaraju et al., 2007), interfere with autophagosome trafficking?

TABLE 2

Quantitation of EGFP-LC3 trafficking data (from FIGS. 3 and 6)

| | Region 1 (R1) (D <2 µm, L <5 µm) | Region 2 (R2) (L >5 µm, Slope <0.5 µm) | Region 3 (R3) (L >5 µm, Slope >0.5 µm) |
|---|---|---|---|
| Control (%) | 87.57 | 6.56 | 5.87 |
| A2E (%)* | 93.51 | 5.37 | 1.12 |
| TSA (%)* | 88.01 | 10.35 | 1.64 |

*significantly different from control cells, p < 0.0001, one-way ANOVA.

Excess Cholesterol Mediates Autophagic Defects in RPE with Bisretinoid

Figures 4A, 4B, 4C, 4D, 4E, 4F, 4G:
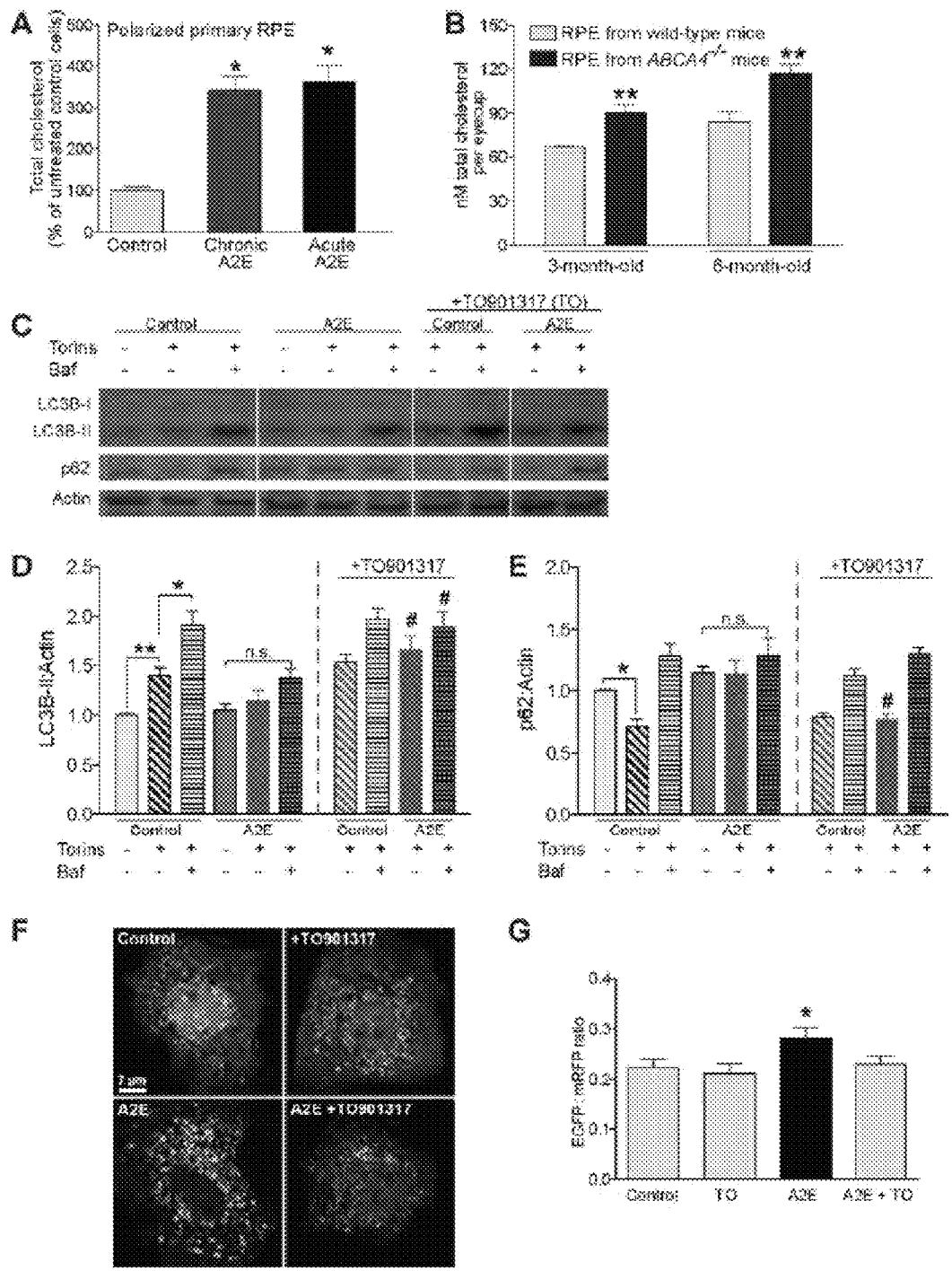
FIG. 4A-G. Cholesterol removal restores autophagosome biogenesis and autophagic flux in RPE with lipofuscin bisretinoids. (A) Biochemical quantification of cholesterol in polarized primary RPE, untreated (control) or exposed to A2E as indicated. Mean±S.E.M., *, p<0.005 relative to controls. (B) Total RPE cholesterol in eyecups from wild-type and ABCA4$^{-/-}$ mice. Mean±S.E.M., n≥9 per group. *, p<0.005 relative to age-matched wild-types. (C) Representative immunoblot of LC3B-I, LC3B-II and p62 protein levels in control or A2E-laden primary RPE monolayers. Cells were untreated or treated with Torins, bafilomycin (Baf, 100 nM for 2 hours) and/or the LXRα agonist TO901317 (1 μM, 20 hours) as indicated. (D) Quantification of LC3B-II immunoblots, n≥9 per condition; *, p<0.05; **, p<0.01; n.s.—not significant. #, significantly greater than corresponding condition without TO901317 (in red hatched bars), p<0.05. (E) Quantification of p62 immunoblots, n≥9 per condition; *, p<0.05; n.s.—not significant. #, signifi-cantly lesser than corresponding condition without TO901317 (in red hatched bars), p<0.05. (F) Stills from live imaging of mRFP-GFP-LC3 in serum-starved RPE treated as indicated. (G) Quantification of EGFP (green) to mRFP (red) fluorescence in (F). Mean±S.E.M., *, significantly greater than all other treatments, p<0.05.
Figures 5A, 5B, 5C, 5D:
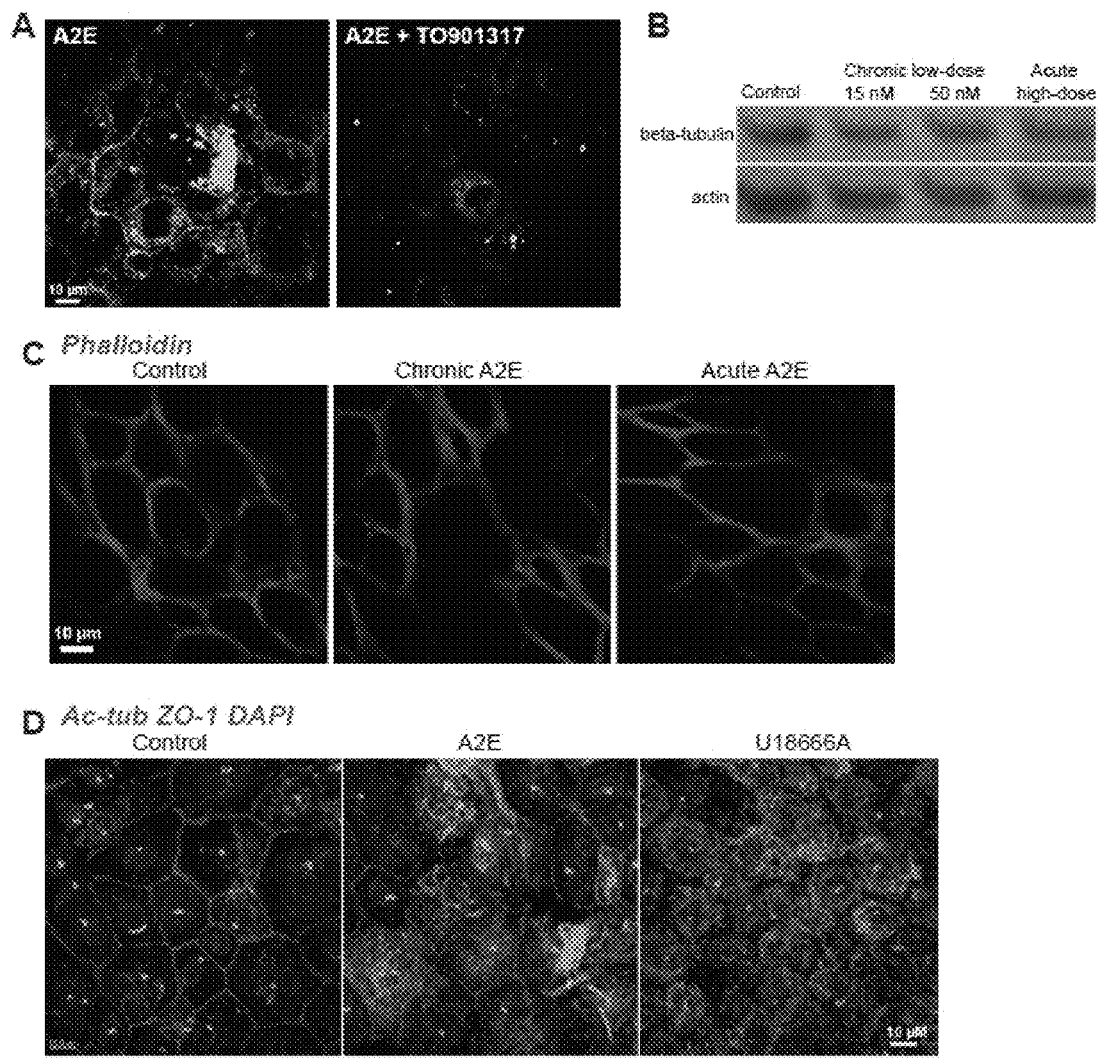
FIG. 5A-D. (A) Filipin staining to detect cholesterol pools in cells treated with A2E or A2E and the LXRα agonist TO901317. Paraformaldehyde-fixed cells were incubated with 50 μg/ml filipin (Sigma) for 45 min at room temperature {Lakkaraju, 2007 #5829}. (B) Expression of beta-tubulin in primary RPE. Lysates from control or A2E-treated (15 nM or 50 nM A2E for three weeks or 20 μM A2E for 6 h) RPE cells were immunoblotted for beta-tubulin and actin. (C) Phalloidin staining of the actin cytoskeleton in polarized primary RPE, control or treated with A2E. (D) Acetylated tubulin staining of RPE untreated (control) or treated with U18666A (1 μM, 16 h) to induce cholesterol storage (Xu et al., 2012).

A critical determinant of organelle motility and fusion is membrane cholesterol (Lebrand et al., 2002; Fraldi et al., 2010). We showed previously that A2E, a cone-shaped lipid, competes with cholesterol (another cone-shaped lipid) for space under the phospholipid umbrella to minimize unfavorable interactions with the aqueous phase. Displacement of cholesterol from the lipid bilayer traps cholesterol within RPE late endosomes and lysosomes (Lakkaraju et al., 2007). A2E and other lipofuscin bisretinoids increased total cell cholesterol measured biochemically in primary RPE after chronic or acute exposure (FIG. 4A) and in the RPE of 3- and 6-month old ABCA4$^{-/-}$ mice (FIG. 4B). We then asked whether A2E-induced cholesterol accumulation was responsible for autophagic defects. To test this, we treated cells with the liver X receptor alpha (LXRα) agonist TO901317, which transcriptionally activates ABCA1 and ABCG1 cholesterol transporters, to clear excess cholesterol in cells with A2E (Lakkaraju et al., 2007) (FIG. 5A). Immunoblotting and quantification of LC3B-II and p62 protein levels after mTOR inhibition showed that TO901317 increased autophagosome biogenesis (FIGS. 4C, 4D) and autophagic flux in A2E-laden cells (FIGS. 4C, 4E). We used live imaging of tfLC3 to follow autophagosome-lysosome fusion: TO901317 restored autophagic flux in cells with A2E and decreased EGFP fluorescence back to control levels (FIGS. 4F, 4G). Collectively, these data confirm that excess cholesterol induces defects in autophagosome trafficking and autophagosome-lysosome fusion in cells with lipofuscin bisretinoids.

Tubulin Acetylation on Stable Microtubules Impairs Autophagosome Trafficking

Figures 6A, 6B, 6C, 6D, 6E, 6F, 6G:
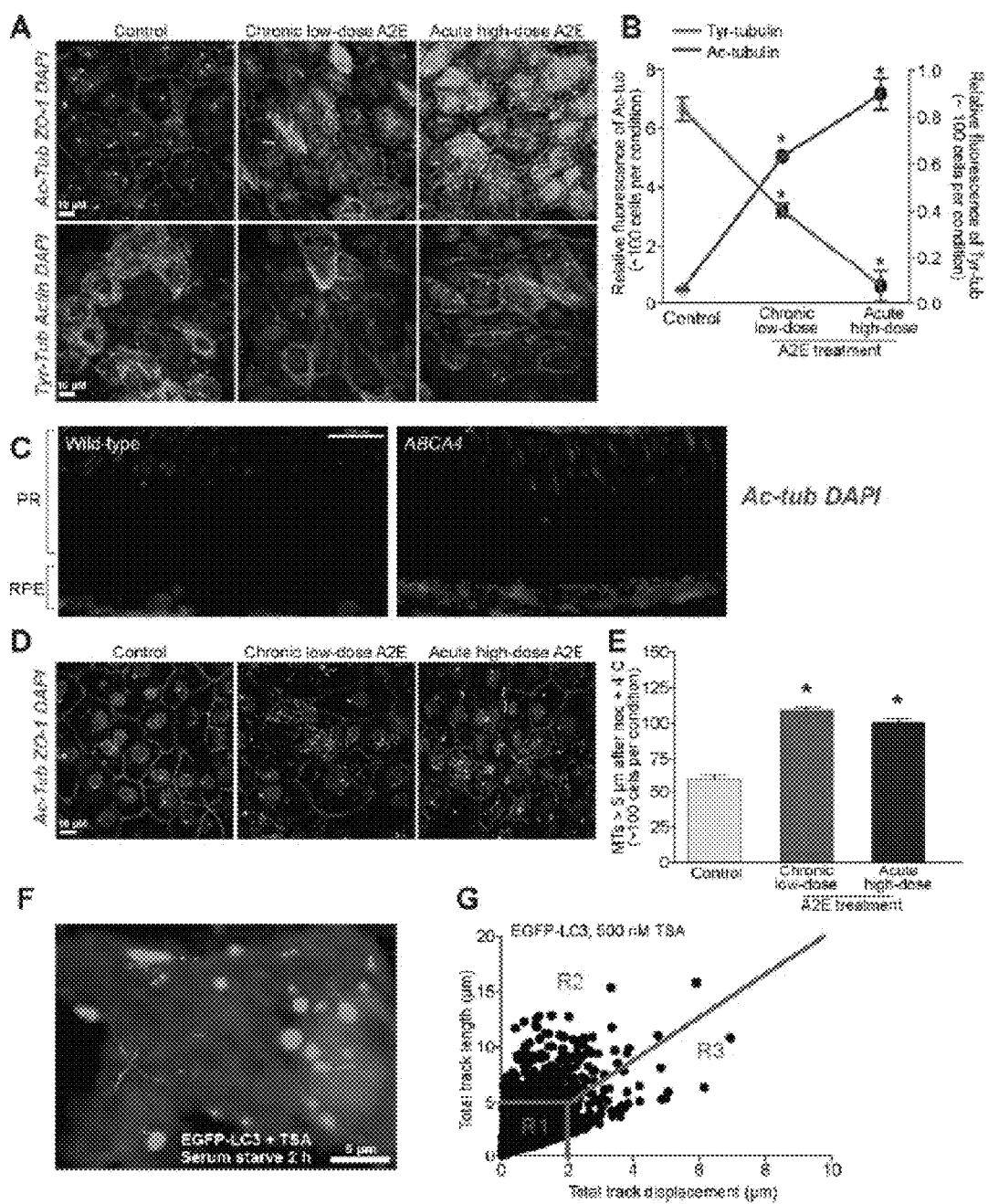
FIG. 6A-G. Tubulin acetylation modulates autophagosome trafficking in the RPE. (A) Immunofluorescence images of polarized primary RPE, untreated or exposed to A2E and stained for acetylated tubulin (green) and ZO-1 (red) or tyrosinated tubulin (green) and phalloidin to label actin (red). (B) Relative intensities of acetylated and tyrosinated tubulin staining in RPE, Mean±S.E.M., *, p<0.0001 relative to corresponding controls. (C) Immunohistochemistry for acetylated tubulin (red) in retinal cryosections from 6-month-old wild-type and ABCA4$^{-/-}$ mice. PR—photoreceptors; RPE—retinal pigment epithelium. Bar: 20 μm. (D) Cells stained for acetylated tubulin (green) and ZO-1 (red) after nocodazole (33 μM) and cold treatment for 30 min. (E) Number of acetylated microtubules longer than 5 μm after nocodazole and cold treatment. Mean±S.E.M., *, p<0.0001. (F) Still from live imaging of EGFP-LC3 trafficking with spots and tracks superimposed in primary RPE treated with the HDAC6 inhibitor trichostatin A (TSA, 500 nM). (G) Track displacement of EGFP-LC3-labeled autophagosomes versus total track length in TSA-treated cells in (F) analyzed by Boolean gating (See Table 2 for values).

Intracellular trafficking is coordinated by the actin and microtubule cytoskeletons and associated motor proteins (Rodriguez-Boulan et al., 2005). Organelle-specific recruitment of microtubule motors is accomplished in part by post-translational modifications of α-tubulin such as acetylation and detyrosination, which preferentially occur on stable microtubules and cause cell type-specific alterations of organelle motility (Joseph et al., 2008; Perdiz et al., 2011). To examine how bisretinoid-induced cholesterol accumulation interferes with autophagy in the RPE, we asked whether altered microtubule stability and/or post-translational tubulin modifications could explain the constrained trafficking of autophagosomes. Immunostaining showed that acetylated tubulin, which is mainly found in primary cilia of control RPE, increased dramatically in cells with A2E, with a corresponding decrease in tyrosinated tubulin (FIGS. 6A, 6B). Neither total α-tubulin expression (FIG. 5B) nor the organization of the actin cytoskeleton (FIG. 5C) were altered in these cells. RPE from 6-month-old ABCA4$^{-/-}$ mice had more acetylated tubulin compared to age-matched wild-types (FIG. 6C), confirming that bis-retinoids increase tubulin acetylation in vivo. Under conditions that depolymerize microtubules in polarized epithelia (nocodazole and cold treatment) (Kreitzer et al., 2003), there were significantly more acetylated microtubules in A2E-laden cells compared to controls (FIGS. 6D, 6E), indicative of increased microtubule stability. Acetylated tubulin also increased in cells treated with U18666A, a drug that induces lysosomal cholesterol storage (Ko et al., 2001) (FIG. 5D), suggesting that cholesterol mediates the effects of A2E on microtubule stability and tubulin acetylation. To establish that hyperacetylation of tubulin disrupts autophagosome traffic, we performed live imaging of EGFP-LC3 trafficking in RPE treated with trichostatin A (TSA), an inhibitor of histone deacetylase 6 (HDAC6), the enzyme that deacetylates tubulin (Joseph et al., 2008). Confirming our hypothesis, TSA treatment replicated the autophagosome trafficking defects seen in cells with A2E (FIGS. 6F, 6G; Table 2). Thus, bisretinoid-induced cholesterol storage prevents autophagosome trafficking by increasing tubulin acetylation.

Figures 7A, 7B, 7C, 7D:
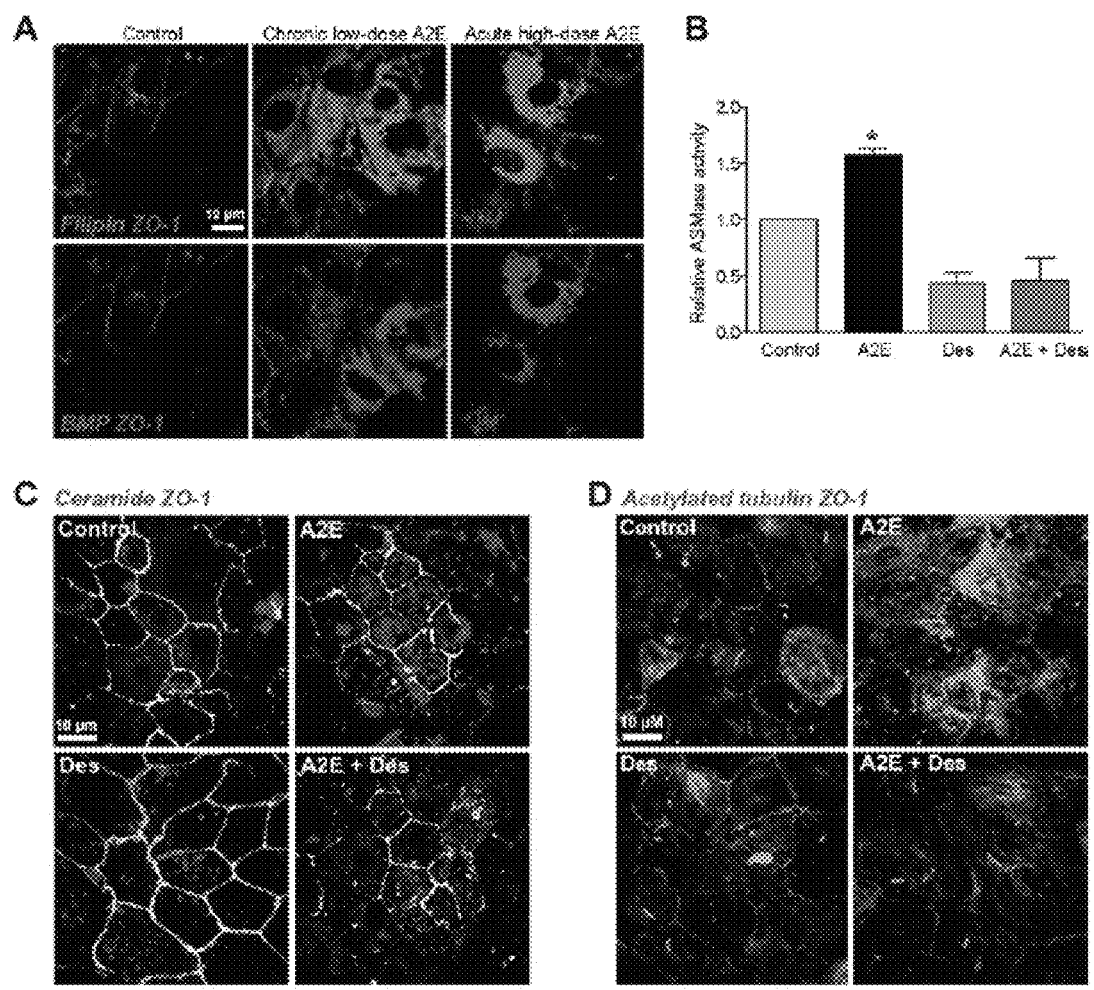
FIG. 7A-D. BMP-mediated activation of ASMase promotes tubulin acetylation. (A) Immunofluorescence images of polarized primary RPE, untreated (Control) or exposed to A2E as indicated, labeled with filipin (blue) and stained for BMP (red) and ZO-1 (purple). (B) ASMase activity in primary RPE untreated (control) or treated with A2E and/or the ASMase inhibitor Desipramine (Des, 10 μM for 3 hours). *, p<0.005 relative to all other conditions, (one-way ANOVA, Dunnett's post-test). (C) Immunofluorescence staining for ceramide (red) and ZO-1 (white) in untreated cells (control) or cells treated with A2E and/or desipramine. (D) Immunofluorescence staining for acetylated tubulin (green) and ZO-1 (red) in untreated cells (control) or cells treated with A2E and/or desipramine.
Figures 8A, 8B, 8C, 8D, 8E:
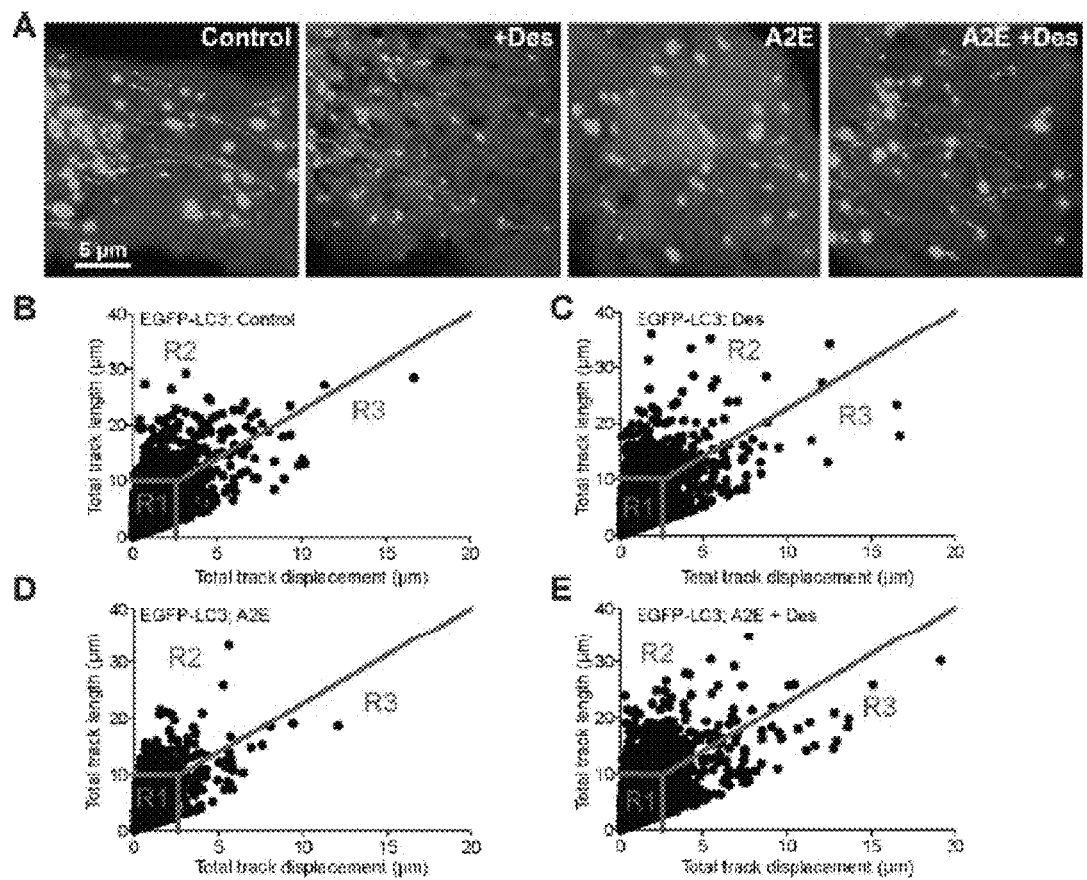
FIG. 8A-E. Desipramine corrects autophagosome trafficking defects in the RPE. (A) Stills from live imaging of EGFP-LC3 with spots and tracks superimposed in serum-starved RPE treated as indicated. Des, desipramine. (B-E) Analyses of live imaging data depicted as track displacement of EGFP-LC3-labeled autophagosomes versus total track length in control cells and cells treated with A2E and/or desipramine. Boolean gating was used to analyze data as explained in the Methods. See Table 3 for R1, R2 and R3 percentages.

Acid Sphingomyelinase Activation Promotes Hyperacetylation of Tubulin in the RPE To dissect the molecular mechanism that links bisretinoid-stimulated cholesterol accumulation in the endo-lysosomal system with tubulin acetylation, we sought clues from cholesterol-storage disorders like Niemann-Pick C1 (NPC1). In NPC1 fibroblasts, excess cholesterol in late endosomes and lysosomes sequesters the anionic phospholipid BMP (Pipalia et al., 2007). BMP is a co-factor for acid sphingomyelinase (ASMase), the lysosomal enzyme that hydrolyzes sphingomyelin to generate ceramide (Kirkegaard et al., 2010). Recent studies show that ceramide regulates tubulin acetylation via atypical protein kinase C (aPKC) and aurora A kinase (He et al., 2012; He et al., 2014). In polarized primary RPE with A2E, immunofluorescence imaging showed high levels of BMP, which co-localized with filipin staining for cholesterol (FIG. 7A). Cells with A2E also had high ASMase activity (FIG. 7B) and more ceramide (FIG. 7C) compared to control RPE. Treatment with desipramine, a functional inhibitor of ASMase (Kornhuber et al., 2010), decreased ASMase activity and ceramide levels (FIGS. 7B, 7C). Desipramine also decreased acetylated tubulin in cells with A2E (FIG. 7D), confirming that cholesterol increases tubulin acetylation via a BMP-ASMase-ceramide pathway.

Inhibition of ASMase Activity Corrects Autophagic Defects in the RPE

Figures 9A, 9B, 9C, 9D, 9E:
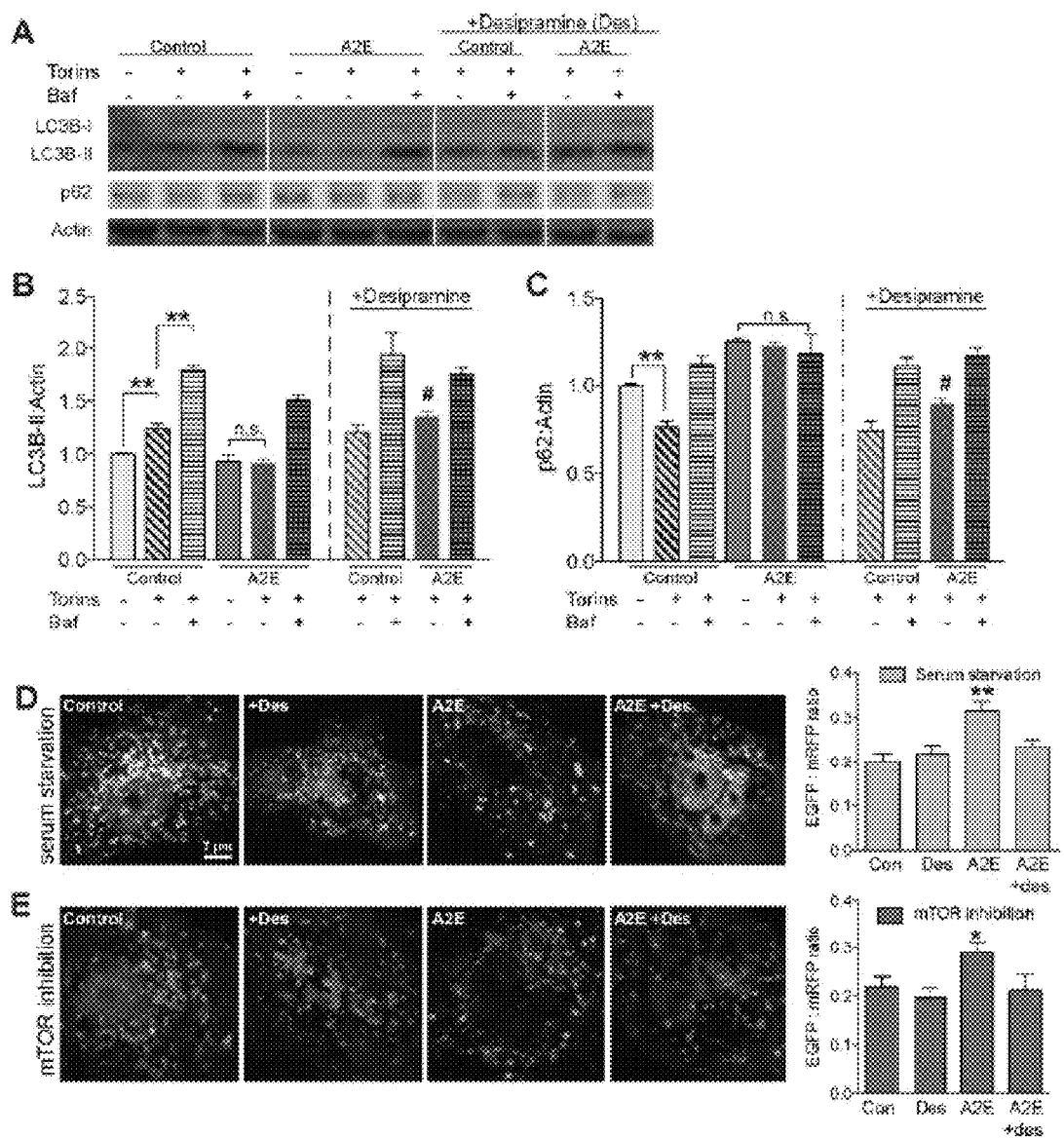
FIG. 9A-E Inhibition of ASMase activity restores autophagic flux in RPE with the lipofuscin bisretinoid A2E. (A) Representative immunoblot of LC3B-I, LC3B-II and p62 protein levels in control or A2E-laden primary RPE monolayers. Cells were untreated or treated with Torins, bafilomycin (Baf, 100 nM for 2 hours) and desipramine (Des, 10 µM, 3 h) as indicated. (B) Quantification of LC3B-II immunoblots, n≥9 per condition; , p<0.01; n.s.— not significant. #, significantly greater than corresponding condition without desipramine (in red hatched bars), p<0.01. (C) Quantification of p62 immunoblots, n≥9 per condition; , p<0.01; n.s.—not significant. #, significantly lesser than corresponding condition without desipramine (in red hatched bars), p<0.001. (D) Stills from live imaging of mRFP-GFP-LC3 and quantification of EGFP/mRFP ratios in serum-starved RPE treated as indicated. **, significantly greater than all other treatments, p<0.0001. (E) Stills from live imaging of tf-LC3 and quantification of EGFP/mRFP ratios in torin-treated RPE treated as indicated. *, significantly greater than all other treatments, p<0.01.

If, as the above data indicate, ASMase is a critical regulator of autophagy, then ASMase inhibition should be sufficient to restore autophagic flux in RPE with bisretinoid-mediated cholesterol accumulation. We first performed live imaging of EFGP-LC3 and image analyses of trafficking data (FIG. 8A) showed that desipramine increased both the number of motile tracks and long-range displacement of autophagosomes in RPE cells with A2E (FIGS. 8B-E, Table 3). After mTOR inhibition, a short exposure to desipramine increased LC3B-II levels in RPE with A2E comparable to those in control cells (FIGS. 9A, 9B). Desipramine also decreased p62 levels in cells with A2E (FIG. 9A, 9C), indicating a restoration of autophagic flux. In agreement with immunoblotting data, tfLC3 imaging showed that desipramine corrected defects in autophagosome-lysosome fusion after serum starvation (FIG. 9D) and Torin treatment (FIG. 9E) in RPE cells with A2E. Thus, ASMase inhibition could be an effective therapeutic target to increase cellular clearance in RPE with lipofuscin bisretinoids.

TABLE 3

Quantitation of EGFP-LC3 trafficking data (from FIG. 8B-E)

|  | Region 1 (R1) (D <2.5 µm, L <10 µm) | Region 2 (R2) (L >10 µm, Slope <0.5 µm) | Region 3 (R3) (L >10 µm, Slope >0.5 µm) |
|---|---|---|---|
| Control | 85.73 | 7.57 | 6.7 |
| Des | 84.28 | 7.79 | 7.93 |
| A2E* | 91.43 | 5.28 | 3.29 |
| A2E + des | 83.88 | 7.77 | 8.35 |

*significantly different from all other conditions, p < 0.0001, one-way ANOVA.

Discussion

Figures 10A, 10B, 10C:
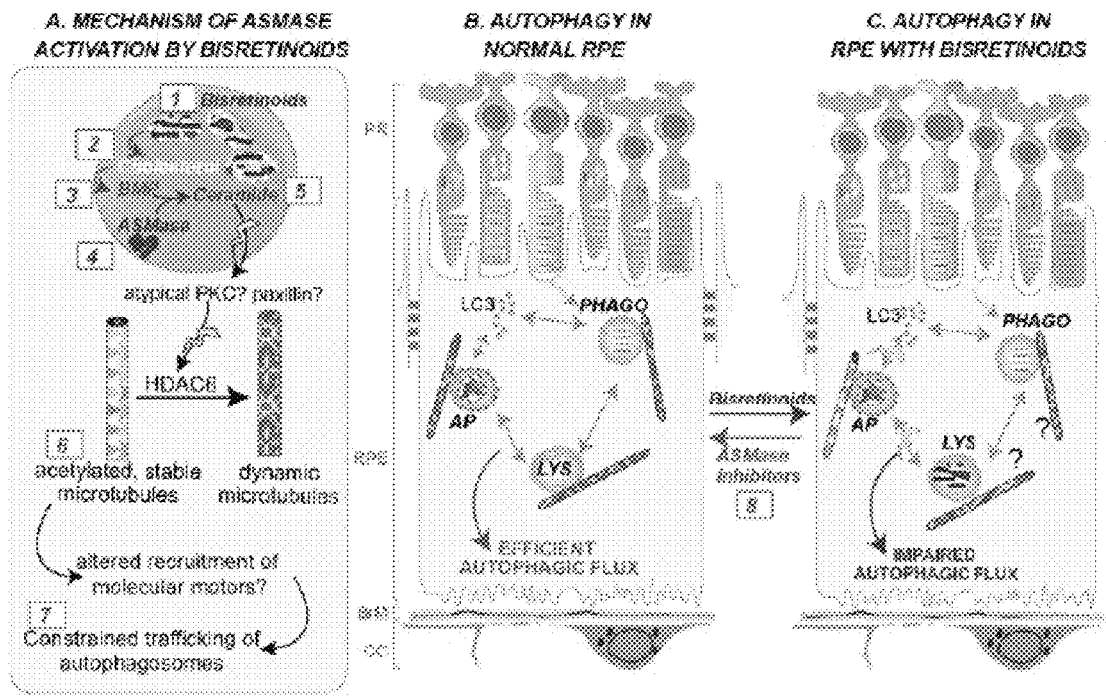
FIG. 10A-C. Model for impaired autophagy in RPE with bisretinoids. (A) Cone-shaped bisretinoids like A2E (#1) sequester cholesterol (#2) in RPE late endosomes and lysosomes, as we have reported previously (Lakkaraju et al., 2007). Data presented in this study show that excess cholesterol in turn traps BMP (#3), which activates ASMase (#4), leading to increased production of ceramide from sphingomyelin (#5). Ceramide promotes tubulin acetylation on stable microtubules (#6) possibly by inhibiting HDAC6. Acetylated microtubules in the RPE interfere with autophagosome motility (#7). (B) In normal RPE, autophagosome biogenesis and transport are essential for efficient autophagic flux. (C) Our data show that in RPE with bisretinoids aberrant activation of ASMase interferes with multiple steps of autophagy by increasing ceramide-induced tubulin acetylation. Whether acetylated microtubules also interfere with the trafficking of other organelles like phagosomes, endosomes and lysosomes is currently under investigation. Drugs that inhibit ASMase decrease tubulin acetylation and increase autophagy in cells with lipofuscin bisretinoids (#8).

Here, we describe a novel molecular mechanism by which autophagy is derailed by lipofuscin bisretinoids and excess cholesterol (FIG. 10), which progressively accumulate in the RPE and contribute to the pathogenesis of macular degenerations (Ambati et al., 2013; Bowes Rickman et al., 2013; Pikuleva and Curcio, 2014). Although decreased autophagy within the retina is thought to participate in the pathogenesis of retinal dystrophies (Bowes Rickman et al., 2013; Frost et al., 2014), little is currently known about the precise mechanisms involved or how autophagy can be exploited as a potential drug target to maintain RPE health.

The data presented in this study identify ASMase as a critical regulator of autophagy in RPE compromised by lipofuscin-mediated cholesterol accumulation. We show that in cells with bisretinoids, cholesterol sequesters the anionic lipid BMP within RPE late endosomes and lysosomes. BMP activates ASMase, the enzyme that hydrolyzes sphingomyelin to ceramide, which in turn promotes tubulin acetylation on stable microtubules. Studies in polarized epithelia and neural progenitors show that ceramide inhibits the microtubule deacetylase HDAC6 by preventing the translocation of aPKC from the membrane to the cytosol. This interferes with aPKC-mediated phosphorylation of two HDAC6 activators, aurora A kinase and glycogen synthase kinase 3β, resulting in the accumulation of acetylated tubulin (He et al., 2012; He et al., 2014). Ceramide can also phosphorylate the focal adhesion scaffold protein paxillin (Sasaki et al., 1996), which has been recently identified as a negative regulator of HDAC6 activity (Deakin and Turner, 2014). Whether any of these mechanisms are responsible for ceramide-induced tubulin acetylation in RPE with bisretinoids remains to be determined.

Live imaging data showed impaired autophagosome biogenesis and trafficking as a consequence of increased tubulin acetylation, either due to lipofuscin bisretinoids or after treatment with the HDAC6 inhibitor TSA. Acetylation is a post-translational modification of α-tubulin that can act either singly or in concert with other modifications such as tyrosination/detyrosination to control motor recruitment in cargo-specific manner (Hammond et al., 2008; Mackeh et al., 2013). Precisely how post-translational modifications of tubulin modulate the trafficking of autophagosomes and other organelles is not well understood. Acetylated microtubules in neurons preferentially recruit kinesin-1 and the scaffolding protein JIP1 (JNK-interacting protein 1) to direct polarized traffic to a subset of neurites (Reed et al., 2006).

Binding of JIP1 to the kinesin heavy chain (KHC) motor domain of kinesin-1 accelerates anterograde traffic, whereas JIP1 binding to the p150$^{Glued}$ subunit of the dynein-dynactin complex promotes retrograde traffic. JIP1 has been recently shown to bind LC3 in neurons to direct dynein-mediated retrograde transport of autophagosomes. Interestingly, the LC3-JIP1 interaction interferes with JIP1-mediated activation of kinesin-1 (Fu et al., 2014). Unlike autophagosomes in neurons, which undergo unidirectional retrograde transport along the axon (Fu et al., 2014), our data show that autophagosomes in the RPE exhibit bidirectional motility, likely driven by opposing actions of kinesin and dynein motors (Fu and Holzbaur, 2014). It is possible that acetylated microtubules in RPE with bisretinoids preferentially recruit kinesin-1 (Reed et al., 2006), which would then compete with LC3 for JIP1 binding (Fu et al., 2014). We also observed fewer tyrosinated microtubules in cells with A2E, which could interfere with the recruitment of p150$^{Glued}$/dynactin (Rocha et al., 2009). Thus, in RPE with bisretinoids, increased acetylation and decreased tyrosination of tubulin could interfere with bidirectional autophagosome transport, possibly by altering the recruitment of motor proteins and/or preventing interactions between motors, scaffolds and cargo. Further studies will help dissect the roles of these motor and scaffolding proteins in directing the transport of autophagosomes and other organelles (endosomes, lysosomes, phagosomes, etc.) in the RPE.

How might increased tubulin acetylation interfere with autophagosome biogenesis? At the earliest stages of autophagosome formation, phosphatidylinositol 3-phosphate binds its effectors WIPI1 and WIPI2 to catalyze the sequential recruitment of Atg proteins that regulate elongation of the preautophagosomal membrane. The fully formed Atg5-Atg12-Atg16L complex induces covalent conjugation of phosphatidylethanolamine to LC3 and facilitates autophagosome closure. Movement of these preautophagosomes along dynamic microtubules is necessary for both Atg recruitment and for driving subsequent steps of autophagosome formation (Geeraert et al., 2010). It is therefore likely that increased stability of acetylated microtubules in cells with A2E interferes with the recruitment of Atg proteins, which decreases membrane elongation and autophagosome biogenesis.

Our data demonstrate that desipramine, a tricyclic antidepressant that increases ASMase proteolysis (Kornhuber et al., 2010), restores autophagy in RPE with A2E by reversing ceramide-induced tubulin acetylation. Thus, functional ASMase inhibitors, many of which are FDA-approved drugs with established safety and efficacy profiles (Kornhuber et al., 2010), are promising candidates for inherited macular dystrophies characterized by elevated levels of lipofuscin bisretinoids such as Stargardt and Best diseases (Travis et al., 2007). Lipofuscin bisretinoids are also implicated in AMD, the most common cause of vision loss in older adults (Ambati et al., 2013). In this context, it is intriguing to note that allelic variants in cholesterol transporters and lipoprotein metabolizing enzymes modulate susceptibility to AMD (Fritsche et al., 2014) and that use of tricyclic antidepressants like desipramine is associated with a statistically significant decrease in the risk of developing early AMD (van Leeuwen et al., 2004). Furthermore, ASMase activity and ceramide levels are increased in the brains of patients with Alzheimer's and Parkinson's diseases (Haughey et al., 2010; Fabelo et al., 2011), which are associated with dysregulated autophagy (Nixon, 2013). It is tempting to speculate that ASMase inhibition could be a novel therapeutic approach not only for retinal degenerations, but also for neurodegenerative diseases.

Example 2. ASMase Inhibition Restores Cell-Surface Complement Regulatory Protein Levels in RPE with Bisretinoids The alternative pathway of the complement system has been implicated in the pathogenesis of AMD. The final step of the complement pathway is the formation of the membrane attack complex (MAC), which forms pores in cell membranes and can cause cell lysis. Lipofuscin and A2E have been shown to activate complement components in mouse models of Stargardt disease and in cultured RPE (Radu et al., 2014; Zhou et al., 2009). The RPE have numerous mechanisms that protect against complement-mediated damage such as (a) cell-surface complement regulatory proteins like CD55, CD59 and CD46, which prevent specific steps of MAC assembly and (b) resealing MAC pores by lysosome exocytosis.

CD55 and CD59 are GPI-anchored proteins whose delivery to the plasma membrane depends on lysosomal cholesterol (Mayor et al., 2004). Cholesterol depletion speeds the transport of CD55 and CD59 to the cell surface by recycling endosomes, whereas cholesterol overload shuttles these GPI-anchored proteins towards lysosomal degradation (Mayor et al., 1998). Since our data show that bisretinoids interfere with long-range microtubule-mediated organelle transport in the RPE, we first examined whether delivery of CD59 is affected in RPE with bisretinoids. Because CD59 prevents MAC formation, we also examined the efficiency of membrane repair by lysosome exocytosis in the RPE after complement attack. Finally, we measured the levels of reactive oxygen species (ROS) in RPE after complement attack because sustained influx of calcium through MAC pores can cause mitochondrial damage and increase ROS generation.

Materials and Methods

Immunostaining

Filter-grown primary polarized RPE were fixed in 2% paraformaldehyde (EMS) for 10 min, blocked in 1% BSA in PBS supplemented with $Ca^{2+}$ and $Mg^{2+}$ and incubated with specific primary antibodies for 1 hour: mouse anti-CD59 (clone MEM43, 1:200, Pierce MA1-19133), rabbit anti-Lamp2a (1:200, Abcam ab18528), goat anti-EEA1 (1:500, Santa Cruz sc-6415), mouse anti-C5b-9 (1:100, Novus NBP1-05120), rabbit anti-C9b/C9 (1:200, Bioss BS-15307R), and rat anti-ZO-1 (1:3000)(23). AlexaFluor secondary antibodies were used at 1:500. Filters were mounted under coverslips on glass slides under VECTASHIELD (Vector labs), sealed and visualized with Andor Revolution XD spinning disk confocal microscope using 60×1.4 NA or 100×1.49 NA oil objectives with identical exposures and gains for each antibody. Quantification of surface CD59 staining was performed using Imaris.

Lysosome Exocytosis

Cells were rinsed in recording medium (HBSS with 4.5 g/L glucose, 20 mM HEPES) and incubated with ionomycin or 1% normal human serum (Quidel) for 10 min at 37° C.

Filters were immediately transferred to ice and analyzed for surface LAMP2 or β-hex activity (see below).

Detection of Cell-Surface Lamp2 and C5b-9

Cells were stained with mouse monoclonal antibody to the lumenal domain of Lamp2 (Serotec, MCA2558, 1:500) (48) or C5b-9 (Novus, NBP1-05120, 1:100) at 4° C. for 30 min. The antibody was diluted in PBS supplemented with $Ca^{2+}$ and $Mg^{2+}$+1% BSA. Cells were then fixed with 2% PFA for 5 min on ice, permeabilized, and stained for ZO-1 as detailed above. Alexa-conjugated secondary antibodies (INVITROGEN) were used at 1:500 for 30 min. Cells were imaged by confocal microscopy (Andor Revolution XD) using a 60× 1.4 NA oil objective. For each set of experiments, the laser power, voltage and offset were identical for a given fluorophore. Quantification of Lamp2 staining was performed by obtaining the total fluorescence using the surface tool in Imaris (Bitplane).

Measurement of β-Hex Activity

After drug treatments, apical and basolateral media were collected, centrifuged at 100×g for 5 min to pellet dead cells and 10,000×g for 5 min to pellet debris. Cells were lysed in 0.5 ml PBS+1% NP-40 for total β-hex activity. To measure enzyme activity, 350 μl of supernatant was incubated for 20 min with 50 μl of 6 mM 4-methyl-umbelliferyl-N-acetyl-β-D-glucosaminide (Sigma) in sodium citrate-phosphate buffer, pH 4.5. Fluorescence was measured after stopping the reaction with 100 μl 2 M Na2CO3, 1.1 M glycine (365 nm excitation, 450 nm emission, Tecan microplate reader). Cell extracts were diluted 1:50 before assay for total cellular β-hex activity.

Reactive Oxygen Species Assay

Reactive oxygen species (ROS) generation was measured using CELLROX Deep Red (Molecular Probes, #10422) according to manufacturer's recommendation. After 10% NHS treatment, medium containing NHS was removed and cells were rinsed with HBSS before incubation in 5 μM CELLROX reagent at 37° C. for 30 min. Cells were rinsed 3 times with PBS and fluorescence was read with microplate reader at Ex/Em of 640/665. For normalization purposes, cells were fixed, stained with DAPI, and fluorescence was read at Ex/Em: 360/460.

Results

Figures 11A, 11B, 11C, 11D, 11E:
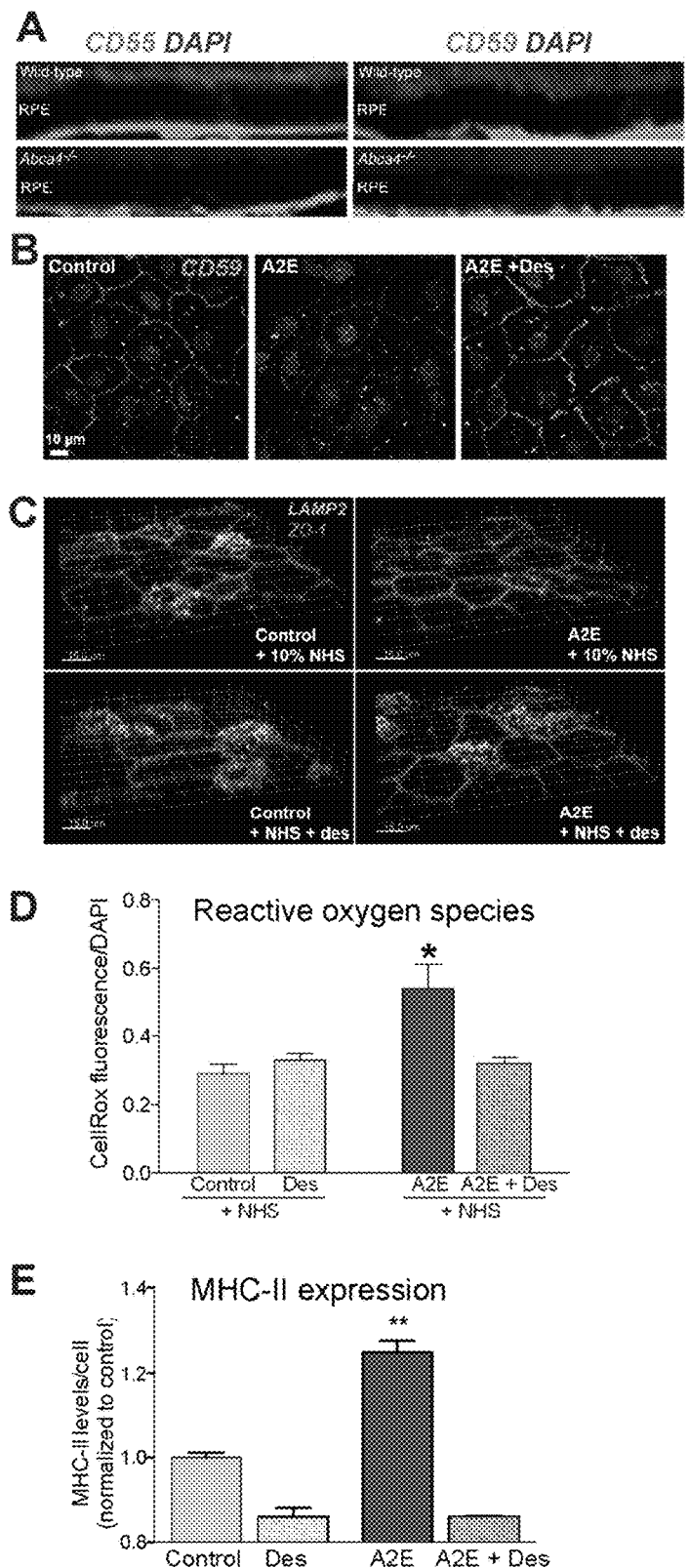
FIG. 11A-E. (A) Expression of GPI-anchored complement regulatory proteins CD55 and CD59 (both green) in retinal cryosections from wild-type or Abca4$^{-/-}$ mice. (B) Surface CD59 staining in polarized primary RPE untreated (control), or exposed to A2E or A2E and desipramine (des). (C) Surface LAMP2 (green) in primary RPE monolayers exposed to 10% normal human serum (NHS) as a source of complement. The tight junction protein ZO-1 is in red. (D) Quantification of reactive oxygen species in primary RPE monolayers exposed to 10% NHS. Beige bars—control RPE; red bars—cells loaded with A2E prior to complement attack. E—Quantification of MHC-II staining. *, p<0.001.

We observed strikingly less CD55 and CD59 on the plasma membrane in RPE from the Abca4$^{-/-}$ mouse model of Stargardt disease (FIG. 11A) and in cells with A2E (FIG. 11B), suggesting that bisretinoid-induced cholesterol storage likely prevents the recycling these GPI-anchored complement-regulatory proteins. Since CD59 inhibits the formation of the membrane attack complex, this would render the RPE susceptible to complement-mediated damage. Lysosome exocytosis reseals pores formed by C5b-9 and prevents cell lysis (Xu et al., 2012). In control RPE monolayers, exposure to 10% normal human serum (NHS) as a source of complement induced lysosome exocytosis monitored by appearance of the lysosomal membrane protein LAMP2 on the cell surface (FIG. 11C, green—LAMP2, red—tight junction protein ZO-1 to demarcate cell boundaries). Lysosome exocytosis was severely blunted in cells with A2E after complement exposure. This inhibition of membrane repair resulted in increased production of ROS in RPE with A2E (FIG. 11D). A short treatment with desipramine increased surface CD59 levels, restored lysosome exocytosis and decreased ROS levels after complement attack (FIGS. 11A, 11C & D). The RPE are antigen-presenting cells and expression of major histocompatibility complex II (MHC-II) in the RPE and outer retina is increased in inflammatory conditions and in AMD (Penfold et al., 1997). Desipramine decreased MHC-II protein levels in the RPE with A2E (FIG. 11E).

Conclusion

Thus, lipofuscin bisretinoids appear to promote a pro-inflammatory environment in the RPE and retina in vivo and our data support the hypothesis that ASMase inhibition is a valid strategy to decrease inflammation in the RPE.

Example 3. Genetic Validation of ASMase as a Therapeutic Target in RPE with Bisretinoids To establish that inhibition of ASMase does indeed decrease tubulin acetylation and increase autophagy in RPE with bisretinoids, we used shRNA-mediated knockdown of ASMase.

Materials and Methods: Primary porcine RPE were transfected with plasmids expressing RFP-tagged shRNA constructs (Origene) to porcine ASMase (SMPD1 gene) and exposed to A2E 48 h after transfection as described previously. Cells were fixed 48 h after A2E loading and stained for acetylated tubulin or LC3 to label autophagosomes. Protein knockdown was confirmed by immunoblotting for ASMase.

Figures 12A, 12B, 12C:
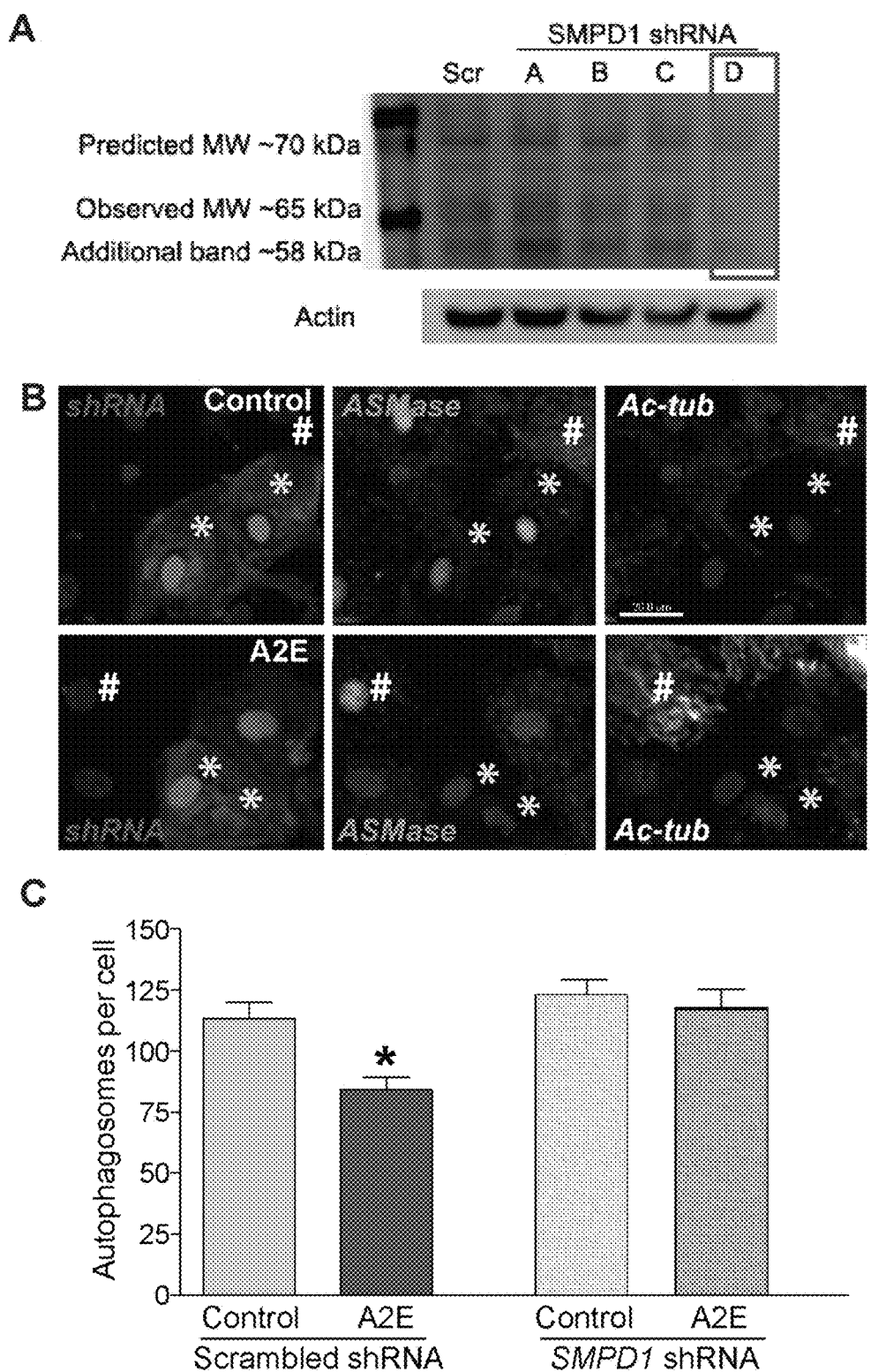
FIG. 12A-C. (A) shRNA-mediated knockdown of ASMase (SMPD1 gene) in primary RPE. Construct D is the most effective. (B) Immunostaining for ASMase (green) and acetylated tubulin (white) in cells expressing shRNA to ASMase (red). Yellow asterisk denotes transfected cells in which ASMase has been knocked down. White # indicate untransfected cells that served as internal controls for comparison. (C) LC3-labeled autophagosomes per cell after scrambled or SMPD1 shRNA transfection. *, significantly lower than all other conditions, p<0.05.

Results: We tested 4 different shRNA constructs and found that construct D elicited the most robust knockdown of ASMase in porcine RPE (FIG. 12A). Similar to our data with desipramine, depletion of ASMase decreased acetylated tubulin in RPE with bisretinoids (FIG. 12B). Compare immunostaining for ASMase (green) and acetylated tubulin (white) in shRNA-expressing cells (RFP-positive, yellow asterisk) with those not transfected (white #). ASMase depletion increased autophagosome biogenesis in RPE with A2E to control levels whereas the scrambled shRNA sequence had no effect (FIG. 12C).

Example 4. Evaluation of ASMase Inhibitors in an in Vitro Model of RPE Dysfunction ASMase is a soluble, zinc-dependent enzyme that binds the lumenal surface of lysosomal membranes to hydrolyze sphingomyelin to ceramide. Rational design of potent, selective ASMase inhibitors is challenging because the crystal structure of the enzyme has not yet been resolved. Desipramine and other cationic amine drugs act as functional ASMase inhibitors: they inhibit binding of ASMase to the anionic lipid BMP, which is required for ASMase activity (Kirkegaard, et al., 2010). When ASMase can no longer bind BMP, it detaches from the lysosomal membrane and becomes susceptible to lysosomal proteolysis (Kolzer, et al., 2004). Therefore, the efficacy of functional ASMase inhibitors depends on their ability to accumulate in lysosomes.

All functional ASMase inhibitors identified thus far are low molecular weight (<500 Da) lipophilic weak bases, with at least one basic nitrogen atom. Although pKa and lipophilicity are important, not all lipophilic weak bases are ASMase inhibitors; structure-activity relationship models show that the steric hindrance of the protonated nitrogen is more important than pKa because it shields the enzyme from binding BMP[42]. Several bisphosphonates such as zoledronic acid, currently used to treat osteoporosis, inhibit ASMase structurally by forming active complexes with the $Zn^{2+}$ ion in the active center of the enzyme[62]. It is thought that structural inhibitors can inhibit ASMase at lower concentrations than functional inhibitors.

Here, we tested the abilities of functional and structural ASMase inhibitors (Table 4) to decrease acetylated tubulin and induce autophagy in our well-characterized polarized primary adult RPE model (Toops, et al. 2014) in the presence of lipofuscin bisretinoids.

Materials and Methods

Figures 13A, 13B, 13C:
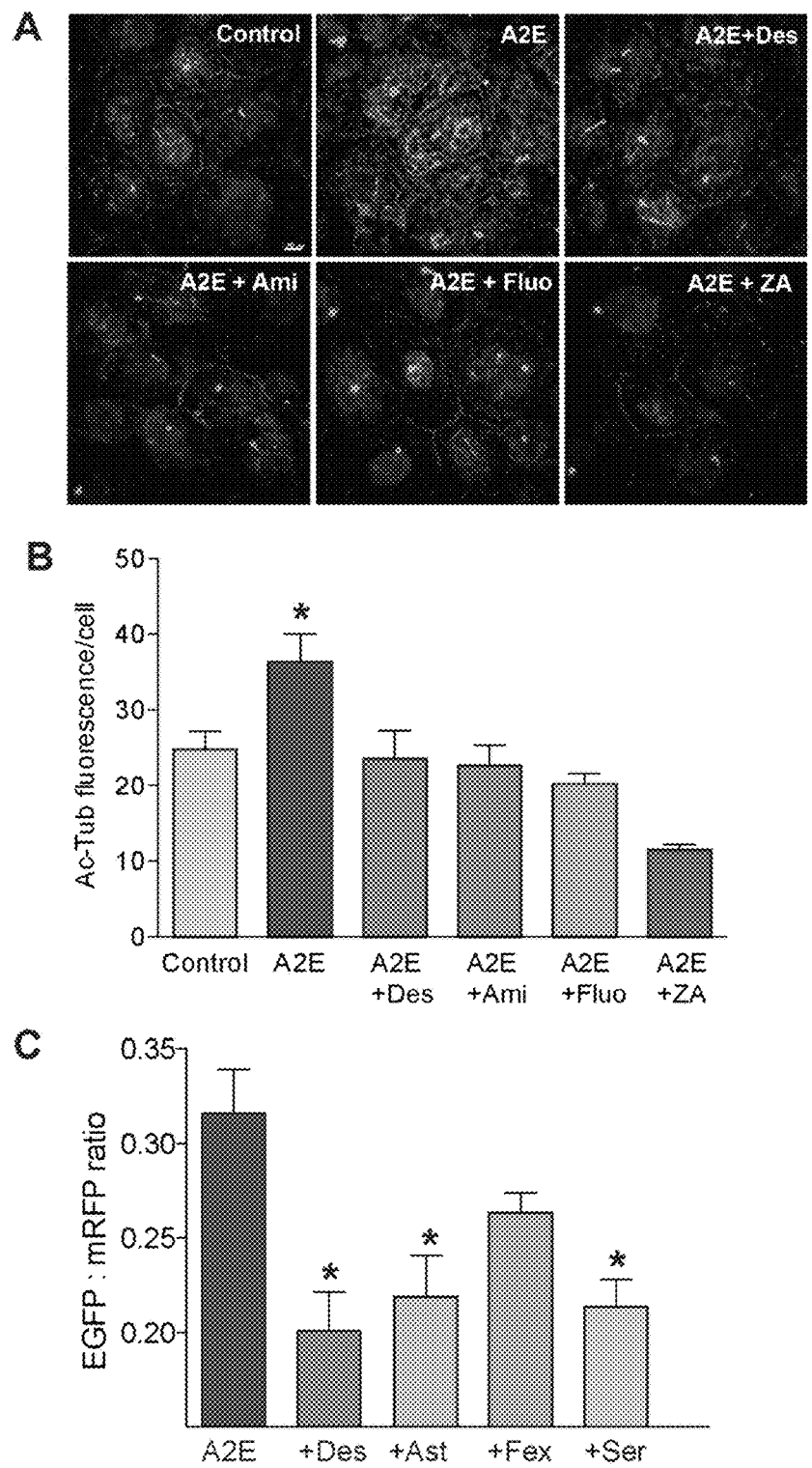
FIG. 13A-C. (A) Acetylated tubulin (green) staining in cells treated with A2E and ASMase inhibitors desipramine (des), amitriptyline (ami), fluoxetine (fluo) or zoledronic acid (ZA). All 10 µM for 3 h, 48 h after A2E treatment. (B) Quantification of acetylated tubulin fluorescence in A. (C) EGFP:mRFP ratios as a measure of tfLC3 flux in primary RPE. *, significantly lower than cells treated with A2E alone, p<0.001; ASMase inhibitors tested include: astemizole (Ast), sertraline (Ser), desipramine (Des), and fexofenadine (Fex).

We performed two initial screens: first, we compared the ability of functional inhibitors (fluoxetine and amitriptyline) with that of the lone structural ASMase inhibitor zoledronic acid in decreasing acetylated tubulin. Here, polarized RPE monolayers with or without A2E were treated with one of the three inhibitors (10 µM, 3 h). Desipramine as a positive control. At the end of the incubation period, cells were fixed and stained for acetylated tubulin, imaged and the amount of acetylated tubulin in the cells was quantified. Second, we evaluated three additional drugs (sertraline, astemizole and fexofenadine) for their abilities to increase autophagy in the RPE. Cells with or without bisretinoids were transfected with mRFP-GFP-LC3, starved to induce autophagy, treated with drugs and imaged as in FIG. 9D.

effective as desipramine in decreasing acetylated tubulin in cells with bisretinoids (FIG. 13A). At an equivalent dose, zoledronic acid appears to be more effective than the functional inhibitors, suggesting that structural ASMase inhibitors could improve RPE function at lower doses than functional inhibitors. Fexofenadine is not as effective as astemizole, sertraline or desipramine in increasing autophagic flux in the RPE. Although astemizole is an effective ASMase inhibitor, it is no longer marketed because of rare cardiovascular side-effects. Our data indicate that astemizole and fexofenadine can be excluded from this list. Further, clomiphene, maprotiline and promethazine will also likely be excluded due to serious side effects. Based on these results, five to seven additional ASMase inhibitors may prove to be as effective as desipramine in increasing autophagy and decreasing inflammation in the RPE. Since zoledronic acid acts by a different mechanism than functional inhibitors and dramatically decreases acetylated tubulin in RPE with bisretinoids, combination therapy with structural and functional inhibitors could prove to be very efficacious in maintaining RPE health and preventing vision loss.

REFERENCES

Ambati, J., Atkinson, J. P., and Gelfand, B. D. (2013). Immunology of age-related macular degeneration. Nat Rev Immunol 13, 438-451.

TABLE 4

FDA-approved ASMase inhibitors.

| Drug* | Current indication | Bulk supplier | Potential issues |
|---|---|---|---|
| Desipramine | Tricyclic antidepressant (TCA); tertiary amine | TOCRIS | |
| Amitriptyline | TCA (tertiary amine) | Selleck Chem | |
| Amlodipine | Calcium channel blocker | TOCRIS | |
| Astemizole | H2-receptor antagonist | TOCRIS | |
| Benzatropine | Anti-cholinergic | SIGMA-ALDRICH | |
| Citalopram | Selective serotonin reuptake inhibitor (SSRI) | TOCRIS | Can cause arrhythmia at high doses. |
| Clomiphene | Selective estrogen receptor modulator | Selleck Chem | May have serious side effects. |
| Cloperastine | Cough suppressant (anti-histamine) | SIGMA-ALDRICH | |
| Cyclobenzaprine | Skeletal muscle relaxant | SIGMA-ALDRICH | |
| Cyproheptadine | Histamine H1 antagonist | TOCRIS | |
| Diphenhydramine | Histamine H1 antagonist | TOCRIS | |
| Fexofenadine | Histamine H1 antagonist | TOCRIS | |
| Fluoxetine | SSRI | TOCRIS | |
| Maprotiline | Tetracyclic antidepressant | TOCRIS | Contraindicated in glaucoma |
| Nortriptyline | TCA (secondary amine) | SIGMA-ALDRICH | |
| Paroxetine | SSRI | TOCRIS | |
| Promethazine | Histamine H1 antagonist | SIGMA-ALDRICH | Contraindicated in glaucoma |
| Sertraline | Selective serotonin reuptake inhibitor | TOCRIS | |
| Zoledronic acid | Bisphosphonate to treat osteoporosis | Enzo Biochem | <4% oral bioavailability |

*All drugs will be used at 0-10 µM for in vitro studies; minimum effective dose established in vitro will be used for ex vivo studies; oral doses may be based on literature reports (e.g., Gulbins et al., 2013).

The effectiveness of ASMase inhibitors is seen in FIG. 13. Our results indicate that fluoxetine and amitriptyline are as Ambati, J., and Fowler, B. J. (2012). Mechanisms of age-related macular degeneration. Neuron 75, 26-39.

Barmada, S. J., Serio, A., Arjun, A., Bilican, B., Daub, A., Ando, D. M., Tsvetkov, A., Pleiss, M., Li, X., Peisach, D., Shaw, C., Chandran, S., and Finkbeiner, S. (2014). Autophagy induction enhances TDP43 turnover and survival in neuronal ALS models. Nat Chem Biol 10, 677-685.

Besirli, C. G., Chinskey, N. D., Zheng, Q. D., and Zacks, D. N. (2011). Autophagy activation in the injured photoreceptor inhibits fas-mediated apoptosis. Invest Ophthalmol Vis Sci 52, 4193-4199.

Bok, D. (1993). The retinal pigment epithelium: a versatile partner in vision. J Cell Sci Suppl 17, 189-195.

Bowes Rickman, C., Farsiu, S., Toth, C. A., and Klingeborn, M. (2013). Dry age-related macular degeneration: mechanisms, therapeutic targets, and imaging. Invest Ophthalmol Vis Sci 54, ORSF68-80.

Chen, Y., Sawada, O., Kohno, H., Le, Y. Z., Subauste, C., Maeda, T., and Maeda, A. (2013). Autophagy protects the retina from light-induced degeneration. J Biol Chem 288, 7506-7518.

Choi, A. M., Ryter, S. W., and Levine, B. (2013). Autophagy in human health and disease. N Engl J Med 368, 651-662.

Codogno, P., Mehrpour, M., and Proikas-Cezanne, T. (2012). Canonical and non-canonical autophagy: variations on a common theme of self-eating? Nat Rev Mol Cell Biol 13, 7-12.

Deakin, N. O., and Turner, C. E. (2014). Paxillin inhibits HDAC6 to regulate microtubule acetylation, Golgi structure, and polarized migration. J Cell Biol 206, 395-413.

Doyle, S. L., Ozaki, E., Brennan, K., Humphries, M. M., Mulfaul, K., Keaney, J., Kenna, P. F., Maminishkis, A., Kiang, A. S., Saunders, S. P., Hams, E., Lavelle, E. C., Gardiner, C., Fallon, P. G., Adamson, P., Humphries, P., and Campbell, M. (2014). IL-18 attenuates experimental choroidal neovascularization as a potential therapy for wet age-related macular degeneration. Sci Transl Med 6, 230ra244.

Eldred, G. E., and Lasky, M. R. (1993). Retinal age pigments generated by self-assembling lysosomotropic detergents. Nature 361, 724-726.

Fabelo, N., Martin, V., Santpere, G., Marin, R., Torrent, L., Ferrer, I., and Diaz, M. (2011). Severe alterations in lipid composition of frontal cortex lipid rafts from Parkinson's disease and incidental Parkinson's disease. Molecular medicine 17, 1107-1118.

Fraldi, A., Annunziata, F., Lombardi, A., Kaiser, H. J., Medina, D. L., Spampanato, C., Fedele, A. O., Polishchuk, R., Sorrentino, N. C., Simons, K., and Ballabio, A. (2010). Lysosomal fusion and SNARE function are impaired by cholesterol accumulation in lysosomal storage disorders. EMBO J 29, 3607-3620.

Fritsche, L. G., Fariss, R. N., Stambolian, D., Abecasis, G. R., Curcio, C. A., and Swaroop, A. (2014). Age-Related Macular Degeneration: Genetics and Biology Coming Together Annu Rev Genomics Hum Genet.

Frost, L. S., Mitchell, C. H., and Boesze-Battaglia, K. (2014). Autophagy in the eye: Implications for ocular cell health. Exp Eye Res.

Fu, M. M., and Holzbaur, E. L. (2014). Integrated regulation of motor-driven organelle transport by scaffolding proteins. Trends Cell Biol.

Fu, M. M., Nirschl, J. J., and Holzbaur, E. L. (2014). LC3 binding to the scaffolding protein JIP1 regulates processive dynein-driven transport of autophagosomes. Dev Cell 29, 577-590.

Geeraert, C., Ratier, A., Pfisterer, S. G., Perdiz, D., Cantaloube, I., Rouault, A., Pattingre, S., Proikas-Cezanne, T., Codogno, P., and Pous, C. (2010). Starvation-induced hyperacetylation of tubulin is required for the stimulation of autophagy by nutrient deprivation. J Biol Chem 285, 24184-24194.

Grumati, P., Coletto, L., Sabatelli, P., Cescon, M., Angelin, A., Bertaggia, E., Blaauw, B., Urciuolo, A., Tiepolo, T., Merlini, L., Maraldi, N. M., Bernardi, P., Sandri, M., and Bonaldo, P. (2010). Autophagy is defective in collagen VI muscular dystrophies, and its reactivation rescues myofiber degeneration. Nat Med 16, 1313-1320.

Gulbins, E. et al. Acid sphingomyelinase-ceramide system mediates effects of antidepressant drugs. *Nat Med* 19, 934-938 (2013).

Haji Abdollahi, S., Hirose, T., 2013. Stargardt-Fundus flavimaculatus: recent advancements and treatment. Semin Ophthalmo128, 372-376.

Hammond, J. W., Cai, D., and Verhey, K. J. (2008). Tubulin modifications and their cellular functions. Curr Opin Cell Biol 20, 71-76.

Haughey, N. J., Bandaru, V. V., Bae, M., and Mattson, M. P. (2010). Roles for dysfunctional sphingolipid metabolism in Alzheimer's disease neuropathogenesis. Biochim Biophys Acta 1801, 878-886.

He, Q., Wang, G., Dasgupta, S., Dinkins, M., Zhu, G., and Bieberich, E. (2012). Characterization of an apical ceramide-enriched compartment regulating ciliogenesis. Mol Biol Cell 23, 3156-3166.

He, Q., Wang, G., Wakade, S., Dasgupta, S., Dinkins, M., Kong, J. N., Spassieva, S. D., and Bieberich, E. (2014). Primary cilia in stem cells and neural progenitors are regulated by neutral sphingomyelinase 2 and ceramide. Mol Biol Cell 25, 1715-1729.

Jimenez-Sanchez, M., Menzies, F. M., Chang, Y. Y., Simecek, N., Neufeld, T. P., and Rubinsztein, D. C. (2012). The Hedgehog signalling pathway regulates autophagy. Nat Commun 3, 1200.

Joseph, R. A., Shepard, B. D., Kannarkat, G. T., Rutledge, T. M., Tuma, D. J., and Tuma, P. L. (2008). Microtubule acetylation and stability may explain alcohol-induced alterations in hepatic protein trafficking Hepatology 47, 1745-1753.

Kim, J. Y., Zhao, H., Martinez, J., Doggett, T. A., Kolesnikov, A. V., Tang, P. H., Ablonczy, Z., Chan, C. C., Zhou, Z., Green, D. R., and Ferguson, T. A. (2013). Noncanonical autophagy promotes the visual cycle. Cell 154, 365-376.

Kirkegaard, T., Roth, A. G., Petersen, N. H., Mahalka, A. K., Olsen, O. D., Moilanen, I., Zylicz, A., Knudsen, J., Sandhoff, K., Arenz, C., Kinnunen, P. K., Nylandsted, J., and Jaattela, M. (2010). Hsp70 stabilizes lysosomes and reverts Niemann-Pick disease-associated lysosomal pathology. Nature 463, 549-553.

Klein, R., Klein, B. E., Jensen, S. C., Cruickshanks, K. J., Lee, K. E., Danforth, L. G., Tomany, S. C., 2001. Medication use and the 5-year incidence of early age-related maculopathy: the Beaver Dam Eye Study. Arch Ophthalmol 119, 1354-1359.

Klionsky, D. J., et al. (2012). Guidelines for the use and interpretation of assays for monitoring autophagy. Autophagy 8, 445-544.

Ko, D. C., Gordon, M. D., Jin, J. Y., and Scott, M. P. (2001). Dynamic movements of organelles containing Niemann-Pick C1 protein: NPC1 involvement in late endocytic events. Mol Biol Cell 12, 601-614.

Koga, H., Kaushik, S., and Cuervo, A. M. (2010). Altered lipid content inhibits autophagic vesicular fusion. FASEB J 24, 3052-3065.

Kolzer, M., Werth, N., Sandhoff, K., 2004. Interactions of acid sphingomyelinase and lipid bilayers in the presence of the tricyclic antidepressant desipramine. FEBS Lett 559, 96-98.

Kornhuber, J., Tripal, P., Reichel, M., Muhle, C., Rhein, C., Muehlbacher, M., Groemer, T. W., and Gulbins, E. (2010). Functional Inhibitors of Acid Sphingomyelinase (FIASMAs): a novel pharmacological group of drugs with broad clinical applications. Cellular physiology and biochemistry: international journal of experimental cellular physiology, biochemistry, and pharmacology 26, 9-20.

Kreitzer, G., Schmoranzer, J., Low, S. H., Li, X., Gan, Y., Weimbs, T., Simon, S. M., and Rodriguez-Boulan, E. (2003). Three-dimensional analysis of post-Golgi carrier exocytosis in epithelial cells. Nat Cell Biol 5, 126-136.

Kubota, R., Boman, N. L., David, R., Mallikaarjun, S., Patil, S., Birch, D., 2012. Safety and effect on rod function of ACU-4429, a novel small-molecule visual cycle modulator. Retina 32, 183-188.

Kunchithapautham, K., and Rohrer, B. (2007a). Apoptosis and autophagy in photoreceptors exposed to oxidative stress. Autophagy 3, 433-441.

Kunchithapautham, K., and Rohrer, B. (2007b). Autophagy is one of the multiple mechanisms active in photoreceptor degeneration. Autophagy 3, 65-66.

Lakkaraju, A., Finnemann, S. C., and Rodriguez-Boulan, E. (2007). The lipofuscin fluorophore A2E perturbs cholesterol metabolism in retinal pigment epithelial cells. Proc Natl Acad Sci USA 104, 11026-11031.

Le Guezennec, X., Brichkina, A., Huang, Y. F., Kostromina, E., Han, W., and Bulavin, D. V. (2012). Wip1-dependent regulation of autophagy, obesity, and atherosclerosis. Cell Metab 16, 68-80.

Lebrand, C., Corti, M., Goodson, H., Cosson, P., Cavalli, V., Mayran, N., Faure, J., and Gruenberg, J. (2002). Late endosome motility depends on lipids via the small GTPase Rab7. EMBO J 21, 1289-1300.

Lee, J. K., Jin, H. K., Park, M. H., Kim, B. R., Lee, P. H., Nakauchi, H., Carter, J. E., He, X., Schuchman, E. H., and Bae, J. S. (2014). Acid sphingomyelinase modulates the autophagic process by controlling lysosomal biogenesis in Alzheimer's disease. J Exp Med 211, 1551-1570.

Liu, D., Meckel, T., and Long, E. O. (2010). Distinct role of rab27a in granule movement at the plasma membrane and in the cytosol of NK cells. PLoS One 5, e12870.

Lois, N., McBain, V., Abdelkader, E., Scott, N. W., Kumari, R., 2013. Retinal pigment epithelial atrophy in patients with exudative age-related macular degeneration undergoing anti-vascular endothelial growth factor therapy. Retina 33, 13-22.

Mackeh, R., Perdiz, D., Lorin, S., Codogno, P., and Pous, C. (2013). Autophagy and microtubules—new story, old players. Journal of cell science 126, 1071-1080.

Mata, N. L., J. Weng, and G. H. Travis. 2000. Biosynthesis of a major lipofuscin fluorophore in mice and humans with ABCR-mediated retinal and macular degeneration. *Proc Natl Acad Sci USA*. 97:7154-7159.

Mayor, S. & Riezman, H. Sorting GPI-anchored proteins. *Nat Rev Mol Cell Biol* 5, 110-120 (2004).

Mayor, S., Sabharanjak, S. & Maxfield, F. R. Cholesterol-dependent retention of GPI-anchored proteins in endosomes. *EMBO J* 17, 4626-4638. (1998).

Meleth, A. D., Wong, W. T., Chew, E. Y., 2011. Treatment for atrophic macular degeneration. Curr Opin Ophthalmol 22, 190-193.

Nixon, R. A. (2013). The role of autophagy in neurodegenerative disease. Nat Med 19, 983-997.

Pampliega, O, Orhon, I., Patel, B., Sridhar, S., Diaz-Carretero, A., Beau, I., Codogno, P., Satir, B. H., Satir, P., and Cuervo, A. M. (2013). Functional interaction between autophagy and ciliogenesis. Nature 502, 194-200.

Perdiz, D., Mackeh, R., Pous, C., and Baillet, A. (2011). The ins and outs of tubulin acetylation: more than just a post-translational modification? Cell Signal 23, 763-771.

Pikuleva, I. A., and Curcio, C. A. (2014). Cholesterol in the retina: The best is yet to come. Prog Retin Eye Res.

Pipalia, N. H., Hao, M., Mukherjee, S., and Maxfield, F. R. (2007). Sterol, protein and lipid trafficking in Chinese hamster ovary cells with Niemann-Pick type C1 defect. Traffic 8, 130-141.

Polson, H. E., de Lartigue, J., Rigden, D. J., Reedijk, M., Urbe, S., Clague, M. J., and Tooze, S. A. (2010). Mammalian Atg18 (WIPI2) localizes to omegasome-anchored phagophores and positively regulates LC3 lipidation. Autophagy 6, 506-522.

Radu, R. A., Hu, J., Yuan, Q., Welch, D. L., Makshanoff, J., Lloyd, M., McMullen, S., Travis, G. H., and Bok, D. (2011). Complement system dysregulation and inflammation in the retinal pigment epithelium of a mouse model for Stargardt macular degeneration. J Biol Chem 286, 18593-18601.

Radu R A, Hu J, Jiang Z, & Bok D (2014) Bisretinoid-mediated complement activation on retinal pigment epithelial cells is dependent on complement factor H haplotype. *J Biol Chem* 289 (13):9113-9120.

Reed, N. A., Cai, D., Blasius, T. L., Jih, G. T., Meyhofer, E., Gaertig, J., and Verhey, K. J. (2006). Microtubule acetylation promotes kinesin-1 binding and transport. Current biology: CB 16, 2166-2172.

Reme, C. E., Wolfrum, U., Imsand, C., Hafezi, F., and Williams, T. P. (1999). Photoreceptor autophagy: effects of light history on number and opsin content of degradative vacuoles. Invest Ophthalmol Vis Sci 40, 2398-2404.

Rocha, N., Kuijl, C., van der Kant, R., Janssen, L., Houben, D., Janssen, H., Zwart, W., and Neefjes, J. (2009). Cholesterol sensor ORP1L contacts the ER protein VAP to control Rab7-RILP-p150 Glued and late endosome positioning. J Cell Biol 185, 1209-1225.

Rodriguez-Boulan, E., Kreitzer, G., and Musch, A. (2005). Organization of vesicular trafficking in epithelia. Nat Rev Mol Cell Biol 6, 233-247.

Rodriguez-Muela, N., Koga, H., Garcia-Ledo, L., de la Villa, P., de la Rosa, E. J., Cuervo, A. M., and Boya, P. (2013). Balance between autophagic pathways preserves retinal homeostasis. Aging Cell 12, 478-488.

Roth, A. G., Drescher, D., Yang, Y., Redmer, S., Uhlig, S., Arenz, C., 2009. Potent and selective inhibition of acid sphingomyelinase by bisphosphonates. Angew Chem Int Ed Engl 48, 7560-7563.

Rubinsztein, D. C., Gestwicki, J. E., Murphy, L. O., and Klionsky, D. J. (2007). Potential therapeutic applications of autophagy. Nat Rev Drug Discov 6, 304-312.

Sarkar, S., Carroll, B., Buganim, Y., Maetzel, D., Ng, A. H., Cassady, J. P., Cohen, M. A., Chakraborty, S., Wang, H., Spooner, E., Ploegh, H., Gsponer, J., Korolchuk, V. I., and Jaenisch, R. (2013). Impaired autophagy in the lipid-storage disorder Niemann-Pick type C1 disease. Cell reports 5, 1302-1315.

Sasaki, T., Hazeki, K., Hazeki, O, Ui, M., and Katada, T. (1996). Focal adhesion kinase (p125FAK) and paxillin are substrates for sphingomyelinase-induced tyrosine phosphorylation in Swiss 3T3 fibroblasts. Biochem J 315 (Pt 3), 1035-1040.

Sparrow, J. R., Gregory-Roberts, E., Yamamoto, K., Blonska, A., Ghosh, S. K., Ueda, K., and Zhou, J. (2012). The bisretinoids of retinal pigment epithelium. Prog Retin Eye Res 31, 121-135.

Sparrow, J. R., C. A. Parish, M. Hashimoto, and K. Nakanishi. 1999. A2E, a lipofuscin fluorophore, in human retinal pigmented epithelial cells in culture. *Invest Ophthalmol Vis Sci.* 40:2988-2995.

Toops, K. A., Tan, L. X., and Lakkaraju, A. (2014). A detailed three-step protocol for live imaging of intracellular traffic in polarized primary porcine RPE monolayers. Exp Eye Res 124C, 74-85.

Toops, K. A., Tan, L. X. & Lakkaraju, A. Differential regulation of organelle dynamics by tubulin acetylation in polarized epithelia. *J Cell Sci* In preparation (2014).

Travis, G. H., Golczak, M., Moise, A. R., and Palczewski, K. (2007). Diseases caused by defects in the visual cycle: retinoids as potential therapeutic agents Annu Rev Pharmacol Toxicol 47, 469-512.

van Leeuwen, R., Tomany, S. C., Wang, J. J., Klein, R., Mitchell, P., Hofman, A., Klein, B. E., Vingerling, J. R., Cumming, R. G., and de Jong, P. T. (2004). Is medication use associated with the incidence of early age-related maculopathy? Pooled findings from 3 continents. Ophthalmology 111, 1169-1175.

Wang, L., Cano, M., and Handa, J. T. (2014). p62 provides dual cytoprotection against oxidative stress in the retinal pigment epithelium. Biochim Biophys Acta 1843, 1248-1258.

Weng, J., Mata, N. L., Azarian, S. M., Tzekov, R. T., Birch, D. G., and Travis, G. H. (1999). Insights into the function of Rim protein in photoreceptors and etiology of Stargardt's disease from the phenotype in abcr knockout mice. Cell 98, 13-23.

Xu, J., Toops, K. A., Diaz, F., Carvajal-Gonzalez, J. M., Gravotta, D., Mazzoni, F., Schreiner, R., Rodriguez-Boulan, E., and Lakkaraju, A. (2012). Mechanism of polarized lysosome exocytosis in epithelial cells. J Cell Sci 125, 5937-5943.

Yao, J., Jia, L., Shelby, S. J., Ganios, A. M., Feathers, K., Thompson, D. A., and Zacks, D. N. (2014). Circadian and Non-Circadian Modulation of Autophagy in Photoreceptors and Retinal Pigment Epithelium. Invest Ophthalmol Vis Sci.

Zhao, C., Yasumura, D., Li, X., Matthes, M., Lloyd, M., Nielsen, G., Ahern, K., Snyder, M., Bok, D., Dunaief, J. L., LaVail, M. M., and Vollrath, D. (2011). mTOR-mediated dedifferentiation of the retinal pigment epithelium initiates photoreceptor degeneration in mice. J Clin Invest 121, 369-383.

Zhou J, Kim S R, Westlund B S, & Sparrow J R (2009) Complement activation by bisretinoid constituents of RPE lipofuscin. *Invest Ophthalmol Vis Sci* 50 (3):1392-1399.

We claim:

1. A method of treating retinal diseases, comprising:
administering an effective amount of a composition comprising desipramine to a retinal disease patient,
wherein at least one of a retinal disease symptom is lessened or progression of the symptom is delayed and wherein the retinal disease is age-related macular degeneration (AMD).

2. The method of claim 1, wherein the disease is associated with an abnormal accumulation of lipofuscin.

3. The method of claim 1, wherein the composition is applied topically to the affected eye or eyes.

4. The method of claim 1, wherein the composition is applied in the following dose range: oral dose of between 10-100 mg/day or topical doses of between 0.1 mg and 1 mg/day.

5. The method of claim 1, wherein the progression of the following symptoms is delayed: accumulation of soft, large drusen; fundus autofluorescence; and dark adaptation.

6. A method of treating macular degeneration in a subject in need thereof, comprising:
identifying a subject with macular degeneration; and
administering to the subject a therapeutically effective amount of a composition comprising desipramine.

7. The method of claim 6, wherein the macular degeneration is age-related macular degeneration.

8. A method of treating macular degeneration in a subject in need thereof, comprising the steps of:
identifying a subject with at least one of
a) an accumulation of soft, large drusen,
b) increased fundus autofluorescence, and
c) delayed dark adaptation; and
administering to the subject a therapeutically effective amount of a composition comprising an inhibitor of acid sphingomyelinase activity, wherein the inhibitor is desipramine.

9. The method of claim 8, wherein the composition additionally comprises a second inhibitor of acid sphingomyelinase activity.

10. The method of claim 9, wherein the composition comprises at least one structural inhibitor of acid sphingomyelinase activity and at least one functional inhibitor of acid sphingomyelinase activity.

* * * * *